US010850080B2

(12) United States Patent
Boden, Jr. et al.

(10) Patent No.: US 10,850,080 B2
(45) Date of Patent: Dec. 1, 2020

(54) ELECTRONIC TOOLSET TO LOCATE, READ, ADJUST, AND CONFIRM ADJUSTMENT IN AN IMPLANTABLE BODILY FLUID DRAINAGE SYSTEM WITHOUT RECALIBRATING FOLLOWING ADJUSTMENT

(71) Applicant: Integra LifeSciences Switzerland Sarl, Le Locle (CH)

(72) Inventors: Thomas Boden, Jr., Middleboro, MA (US); Patricia D'Aoust, Franklin, MA (US); Alexander Arazawa, Cambridge, MA (US); Adam Elias, Raleigh, NC (US); William Jacob Ward, Apex, NC (US)

(73) Assignee: Integra LifeSciences Switzerland Sárl, Le Locle (CH)

( * ) Notice: Subject to any disclaimer, the term of this patent is extended or adjusted under 35 U.S.C. 154(b) by 562 days.

(21) Appl. No.: 15/708,404

(22) Filed: Sep. 19, 2017

(65) Prior Publication Data
US 2019/0083762 A1  Mar. 21, 2019

(51) Int. Cl.
*A61M 27/00* (2006.01)
*G01R 33/00* (2006.01)
*G01R 35/00* (2006.01)

(52) U.S. Cl.
CPC ....... *A61M 27/006* (2013.01); *G01R 33/0076* (2013.01); *A61M 2205/103* (2013.01);
(Continued)

(58) Field of Classification Search
CPC .......... A61M 27/006; A61M 2205/103; A61M 2205/3317; A61M 2205/3331;
(Continued)

(56) References Cited

U.S. PATENT DOCUMENTS 3,902,252 A  9/1975  Farber
4,173,228 A  11/1979  Van Steenwyk et al.
(Continued)

FOREIGN PATENT DOCUMENTS

EP  2 826 517  1/2015

OTHER PUBLICATIONS

Copending, co-owned U.S. Appl. No. 15/708,496, filed Sep. 19, 2017.
(Continued)

*Primary Examiner* — Benjamin J Klein
(74) *Attorney, Agent, or Firm* — Cohen & Hildebrand, PLLC

(57) ABSTRACT

A method of using an electronic toolset for locating, reading, adjusting and confirming adjustment of an implantable bodily fluid drainage system without requiring recalibration following adjustment from a current valve setting to a new valve setting using an electronic toolset including an adjustment tool having a magnetic element and an indicator tool including a sensor array. The need to remove the electronic toolset from the patient to recalibrate or zero the sensor array prior to confirming the new valve setting is eliminated. This is realized by disposing a ferromagnetic system component of the indicator tool in a magnet shield cage made of a metallic alloy to prevent magnetic fields produced by a magnetic element in the adjustment tool during the adjusting step from influencing the sensor array.

19 Claims, 22 Drawing Sheets

(52) U.S. Cl.
CPC ............... *A61M 2205/3317* (2013.01); *A61M 2205/3331* (2013.01); *A61M 2205/3515* (2013.01); *A61M 2205/50* (2013.01); *A61M 2205/583* (2013.01); *A61M 2205/6054* (2013.01); *A61M 2205/70* (2013.01); *G01R 35/005* (2013.01)

(58) Field of Classification Search
CPC ...... A61M 2205/3515; A61M 2205/50; A61M 2205/583; A61M 2205/6054; A61M 2205/70; G01R 33/005; G01R 33/0076
See application file for complete search history.

(56) References Cited

U.S. PATENT DOCUMENTS

| | | |
|---|---|---|
| 4,595,390 A | 6/1986 | Hakim et al. |
| 4,608,992 A | 9/1986 | Hakim et al. |
| 4,622,644 A | 11/1986 | Hansen |
| 4,839,809 A | 6/1989 | Leighton et al. |
| 5,309,096 A | 5/1994 | Hoegnelid |
| 5,425,382 A | 6/1995 | Golden et al. |
| 5,438,990 A | 8/1995 | Wahlstrand et al. |
| 5,525,901 A | 6/1996 | Clymer et al. |
| 5,643,194 A | 7/1997 | Negre |
| 5,709,225 A | 1/1998 | Budgifvars et al. |
| 5,758,667 A | 6/1998 | Slettenmark |
| 5,879,297 A | 3/1999 | Haynor et al. |
| 6,101,417 A | 8/2000 | Vogel et al. |
| 6,129,668 A | 10/2000 | Haynor et al. |
| 6,138,681 A | 10/2000 | Chen et al. |
| 6,216,028 B1 | 4/2001 | Haynor et al. |
| 6,242,907 B1 | 6/2001 | Clymer et al. |
| 6,263,230 B1 | 7/2001 | Haynor et al. |
| 6,439,538 B1 | 8/2002 | Ito |
| 6,485,449 B2 | 11/2002 | Ito |
| 6,690,159 B2 | 2/2004 | Burreson et al. |
| 6,702,249 B2 | 3/2004 | Ito |
| 6,707,293 B2 | 3/2004 | Wan et al. |
| 6,850,803 B1 | 2/2005 | Jimenez et al. |
| 6,882,146 B2 | 4/2005 | Maiwald |
| 6,883,241 B2 | 4/2005 | Moskowitz et al. |
| 6,891,367 B2 | 5/2005 | Shinmura et al. |
| 6,937,906 B2 | 8/2005 | Terry et al. |
| 6,951,059 B2 | 10/2005 | Moskowitz et al. |
| 7,126,331 B2 | 10/2006 | Johnson et al. |
| 7,173,419 B1 | 2/2007 | Johnson et al. |
| 7,228,252 B2 | 6/2007 | Alexander et al. |
| 7,301,332 B2 | 11/2007 | Govari et al. |
| 7,334,582 B2 | 2/2008 | Bertrand et al. |
| 7,525,309 B2 | 4/2009 | Sherman et al. |
| 7,753,913 B2 | 7/2010 | Szakelyhidi, Jr. et al. |
| 7,842,004 B2 | 11/2010 | Kassem |
| 7,856,987 B2 | 12/2010 | Bertrand et al. |
| 7,921,571 B2 | 4/2011 | Moureaux et al. |
| 7,945,334 B2 | 5/2011 | Jimenez et al. |
| 8,015,977 B2 | 9/2011 | Bertrand et al. |
| 8,038,641 B2 | 10/2011 | Soares et al. |
| 8,148,978 B2 | 4/2012 | Sherman et al. |
| 8,241,240 B2 | 8/2012 | Murphy |
| 8,257,296 B2 | 9/2012 | Bertrand et al. |
| 8,322,365 B2 | 12/2012 | Wilson et al. |
| 8,398,617 B2 | 3/2013 | Ginggen et al. |
| 8,518,023 B2 | 8/2013 | Roth et al. |
| 8,539,956 B2 | 9/2013 | Bertrand et al. |
| 8,591,499 B2 | 11/2013 | Girardin et al. |
| 8,617,142 B2 | 12/2013 | Wilson et al. |
| 8,622,978 B2 | 1/2014 | Bertrand et al. |
| 8,630,695 B2 | 1/2014 | Negre et al. |
| 8,733,394 B2 | 5/2014 | Negre et al. |
| 8,753,331 B2 | 6/2014 | Murphy |
| 8,862,200 B2 | 10/2014 | Sherman et al. |
| 9,126,010 B2 | 9/2015 | Shah et al. |
| 9,149,615 B2 | 10/2015 | Wilson |
| 9,220,876 B2 | 12/2015 | Girardin et al. |
| 9,242,077 B2 | 1/2016 | Wilson et al. |
| 9,295,826 B2 | 3/2016 | Bertrand et al. |
| 9,364,646 B2 | 6/2016 | Bertrand et al. |
| 9,381,301 B2 | 7/2016 | Lattanzio et al. |
| 9,427,559 B2 | 8/2016 | Shah et al. |
| 9,453,934 B2 | 9/2016 | Hughes |
| 9,585,600 B2 | 3/2017 | Sharonov |
| 2004/0017192 A1 | 1/2004 | Clymer et al. |
| 2004/0055610 A1 | 3/2004 | Forsell |
| 2004/0064030 A1 | 4/2004 | Forsell |
| 2004/0097803 A1 | 5/2004 | Panescu |
| 2004/0250820 A1 | 12/2004 | Forsell |
| 2005/0022403 A1* | 2/2005 | Moskowitz ......... A61M 27/006 33/355 R |
| 2005/0187509 A1 | 8/2005 | Wolf |
| 2006/0124140 A1 | 6/2006 | Forsell |
| 2007/0276218 A1 | 11/2007 | Yellen |
| 2010/0010338 A1 | 1/2010 | van Dam et al. |
| 2010/0292759 A1 | 11/2010 | Hahn et al. |
| 2011/0031961 A1 | 2/2011 | Durand et al. |
| 2011/0105991 A1* | 5/2011 | Roth ................... F16K 37/0041 604/9 |
| 2012/0041297 A1 | 2/2012 | McGary |
| 2012/0302938 A1 | 11/2012 | Browd et al. |
| 2013/0197422 A1 | 8/2013 | Browd et al. |
| 2014/0336560 A1 | 11/2014 | Hakim |
| 2015/0196742 A1 | 7/2015 | Browd et al. |
| 2016/0089519 A1 | 3/2016 | Bittenson |
| 2016/0166813 A1 | 6/2016 | Bertrand et al. |
| 2016/0184563 A1 | 6/2016 | Bertrand et al. |
| 2016/0279396 A1 | 9/2016 | Bertrand et al. |
| 2017/0095650 A1 | 4/2017 | Wilson |
| 2017/0209056 A1 | 7/2017 | Browd et al. |
| 2018/0001064 A1* | 1/2018 | Pfleiderer ........... A61M 27/006 |
| 2018/0015266 A1 | 1/2018 | Amery |
| 2018/0126147 A1 | 5/2018 | Hakim |
| 2018/0184943 A1 | 7/2018 | Boden |
| 2018/0243542 A1 | 8/2018 | Pfleiderer et al. |

OTHER PUBLICATIONS

Copending, co-owned U.S. Appl. No. 15/708,549, filed Sep. 19, 2017.

Copending, co-owned U.S. Appl. No. 15/708,600, filed Sep. 19, 2017.

\* cited by examiner

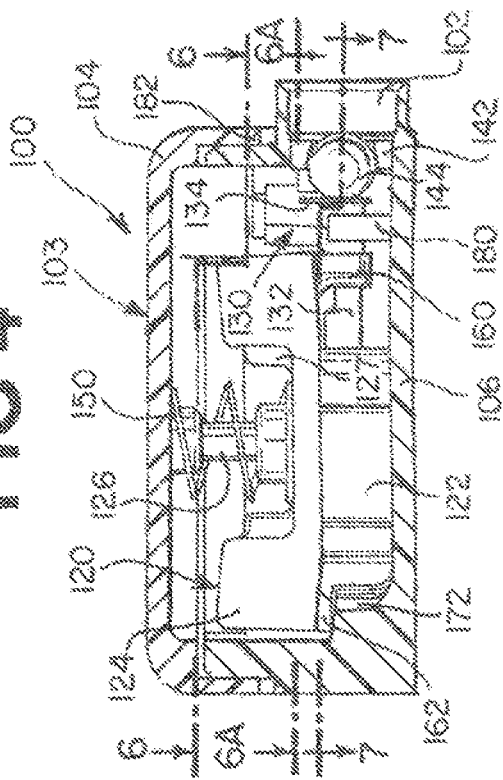
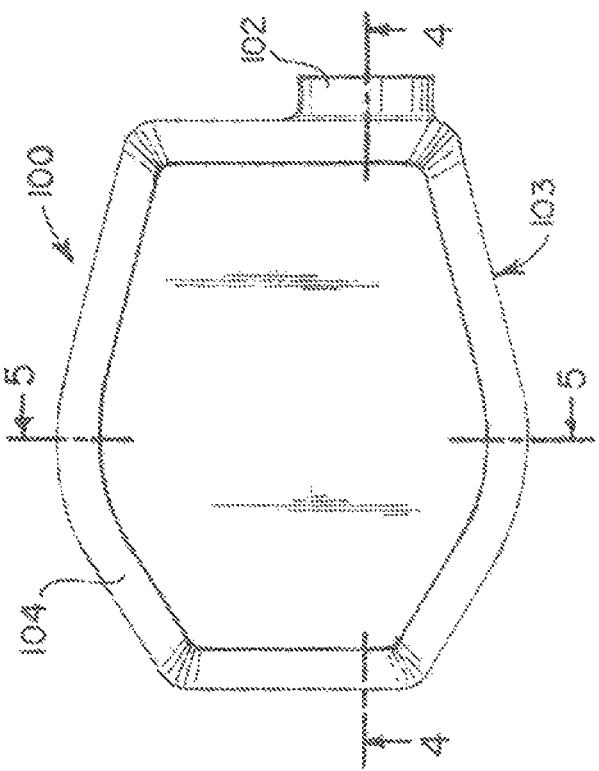

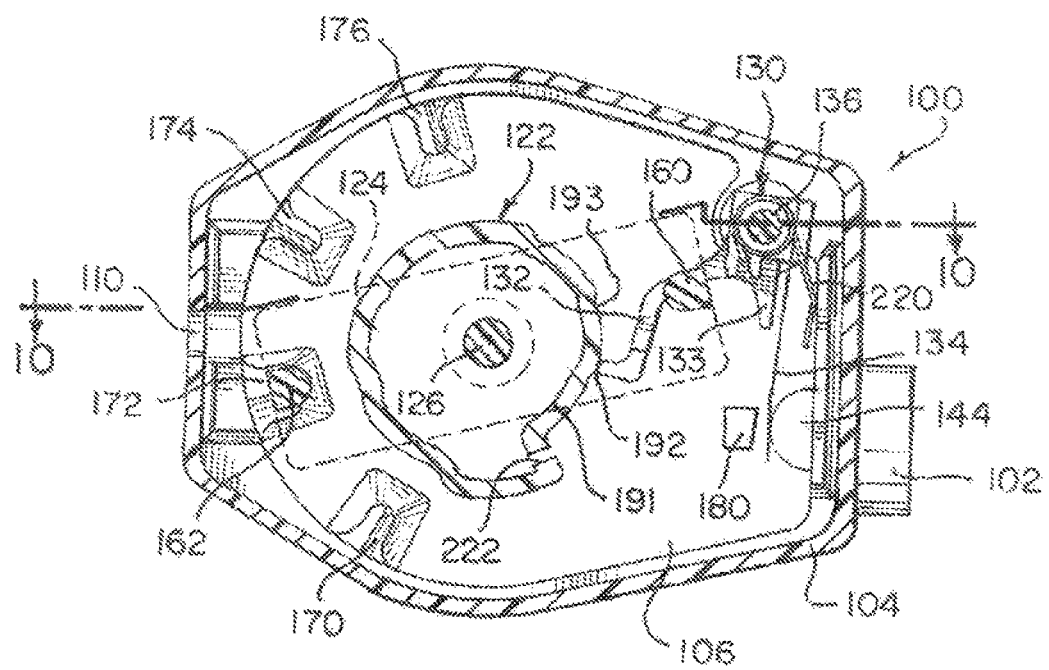

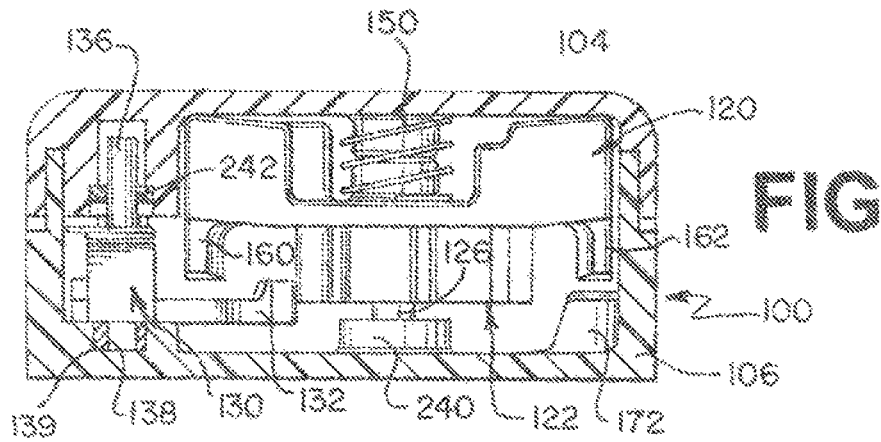
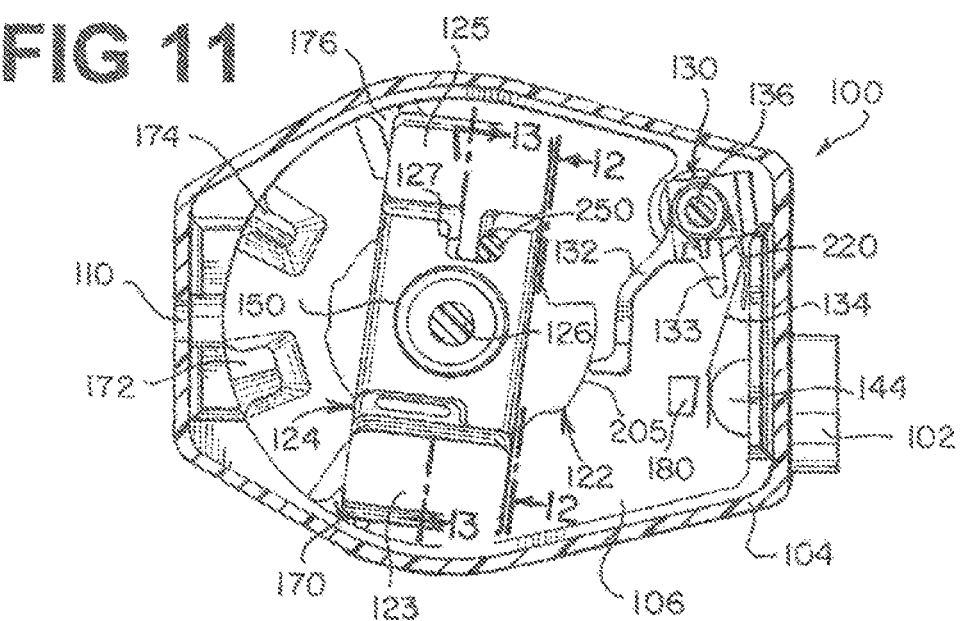
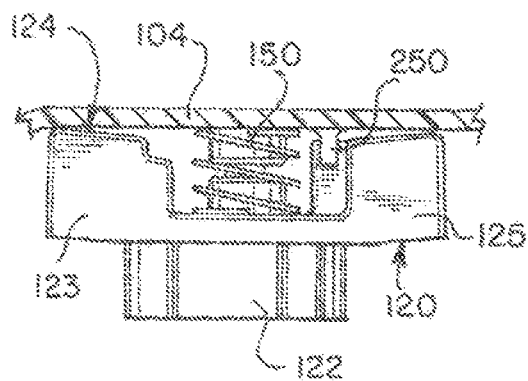

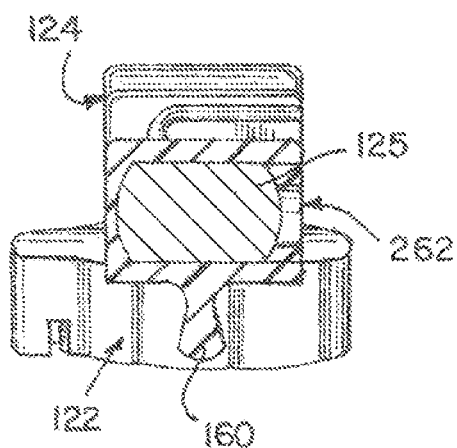

ELECTRONIC TOOLSET TO LOCATE, READ, ADJUST, AND CONFIRM ADJUSTMENT IN AN IMPLANTABLE BODILY FLUID DRAINAGE SYSTEM WITHOUT RECALIBRATING FOLLOWING ADJUSTMENT

BACKGROUND OF THE INVENTION

Field of the Invention

The present invention relates to a system and method for an implantable drainage valve for drainage of a bodily fluid (e.g., cerebrospinal fluid). In particular, the present inventive system and method is directed to an improved electronic tool set for locating, reading, adjusting, and confirming adjustment of an implantable bodily fluid drainage system without requiring the user to remove the toolset from the patient for recalibration/re-zeroing following adjustment.

Description of Related Art

Hydrocephalus is the accumulation of cerebrospinal fluid in the brain, resulting from increased production, or more commonly, pathway obstruction or decreased absorption of the fluid. Cerebrospinal fluid (CSF) shunts have been used for decades for the treatment of hydrocephalus. A CSF shunt involves establishing an accessory pathway for the movement of CSF to bypass an obstruction of the natural pathways.

The shunt is positioned to enable the CSF to be drained from the cerebral ventricles or sub-arachnoid spaces into another absorption site (e.g., the right atrium of the heart or the peritoneal cavity) through a system of small catheters. A regulatory device, such as a valve, may be inserted into the pathway of the catheters. In general, the valve keeps the CSF flowing away from the brain and moderates the pressure or flow rate. The drainage system using catheters and valves enables the excess CSF within the brain to be evacuated and, thereby, the pressure within the cranium to be reduced.

Some implantable valves are fixed pressure valves (i.e., monopressure valves) while others have adjustable or programmable pressure settings. Programmable or adjustable implantable valves are desirable in that the valve pressure setting may be varied non-invasively via an external control device over the course of treatment without requiring explantation. One such conventional adjustable or programmable implantable valve using magnets is the CODMAN® HAKIM® Programmable Valve (CHPV), as disclosed in U.S. Pat. No. 4,595,390, which is assigned to DePuy Orthopedics, a J&J company related to that of the present assignee, and herein incorporated by reference in its entirety. Another programmable implantable drainage valve is the CODMAN CERTAS® Programmable Valve, as disclosed in U.S. Pat. No. 8,322,365, is also assigned to DePuy Orthopedics, a J&J company related to that of the present assignee, and each of which is herein incorporated by reference in its entirety. Medtronic also has a programmable implantable shunt valve Strata® controlled using magnets, as disclosed in U.S. Pat. No. 7,856,987 and herein incorporated by reference in its entirety. Each of these conventional programmable valves includes at least one magnetic element by which the valve setting is adjusted. Specifically, these conventional programmable implantable valves may be non-invasively controlled post-implantation using an electronic toolset that, based on a measured magnetic field produced by the magnet(s) in the valve, can locate, read the current valve setting, adjust the valve setting from a current valve setting to a new valve setting, and confirm the adjusted new valve setting. The electronic toolset varies depending on the particular programmable implantable valve, however, the electronic toolset typically includes: a locator tool for determining the center of the implanted valve; an indicator tool for reading the current valve setting and confirming an adjusted new valve setting; and an adjustment tool for changing the valve setting from a current valve setting to an adjusted new valve setting.

The adjustment tool used to change the valve setting includes one or more magnetic elements (e.g. magnets or electromagnetic coils) of sufficient strength to rotate the magnet(s) associated with the rotating construct in the adjustable valve unit of the programmable implantable valve to a desired setting. Due to the strength of the magnetic elements any residual magnetic field after use of the adjustment tool may result in overload of the sensors that need to be reset or residual magnetism having a deleterious influence on the operation of the other tools in the electronic toolset resulting in a possibly incorrect determination of location of the center of the implantable valve, orientation angle, and/or the reading of the valve setting (e.g., current or adjusted new valve setting). Due to such negative influence of the external magnetic field generated by the magnetic component(s) in the adjustment tool on components within the locator/indicator, following adjustment of the valve setting using the adjustment tool, the medical personnel are required to move the electronic toolset away from the implanted valve, re-zero the device to the environment, re-locate the center and orientation of the implantable valve and then read the new valve setting to confirm that it has been properly adjusted to the desired setting (this is the procedure that must be followed with the Medtronic Strata-Varius® programmable valve). These additional steps lengthen procedural time and increase the risk of human error that could influence proper confirmation of a change in valve setting.

It is therefore desirable to develop an improved electronic toolset used to locate, read, adjust, and confirm successful adjustment in an implantable bodily fluid drainage system that eliminates having to re-zero/recalibrate following adjustment to a new valve setting.

SUMMARY OF THE INVENTION

An aspect of the present invention is directed to an improved electronic toolset used to locate, read, adjust, and confirm successful adjustment in an implantable bodily fluid drainage system that eliminates having to re-zero/recalibrate following adjustment to a new valve setting.

Another aspect of the present invention relates to a method of using an electronic toolset for locating, reading, adjusting and confirming adjustment of an implantable bodily fluid drainage system without requiring recalibration following adjustment. The implantable bodily fluid drainage system includes an implantable bodily fluid drainage valve having an adjustable valve unit. The adjustable valve unit is adjusted from a current valve setting to a new valve setting using an adjustment tool in the electronic toolset, wherein the adjustment tool has at least one magnetic element and an indicator tool in the electronic toolset reads or confirms the current valve setting using a sensor array. The present inventive method eliminates having to remove the electronic toolset from the patient to recalibrate or zero the sensor array prior to confirming the new valve setting adjusted in the adjusting step.

In another aspect of the present invention the indication tool includes a ferromagnetic system component disposed in a magnet shield cage made of a metallic alloy having a permeability $\mu z \geq$ approximately $1.0 \times 10^{-4}$ to prevent magnetic fields produced by the at least one magnetic element in the adjustment tool during the adjusting step from influencing the sensor array.

While yet another aspect of the present invention is directed to an electronic toolset for locating, reading, adjusting and confirming adjustment of an implantable bodily fluid drainage system without requiring recalibration following adjustment, wherein the implantable bodily fluid drainage system comprises an implantable bodily fluid drainage valve having an adjustable valve unit. The electronic toolset includes an adjustment tool having at least one magnetic element for adjusting the adjustable valve unit from a current valve setting to a new valve setting. In addition, the electronic tools also includes an indication tool for reading the current valve setting or confirming a new valve setting using a sensor array. The indication tool further includes a ferromagnetic system component disposed in a magnet shield cage made of a metallic alloy having a permeability $\mu z \geq$ approximately $1.0 \times 10^{-4}$ to prevent residual magnetic fields produced by the plurality of magnets in the adjustment tool from influencing the sensor array.

BRIEF DESCRIPTION OF THE DRAWING

The foregoing and other features of the present invention will be more readily apparent from the following detailed description and drawings of illustrative of the invention wherein like reference numbers refer to similar elements throughout the several views and in which:

FIG. 3 is a top view of the adjustable valve unit of FIG. 2;

FIG. 4 is a side cross-sectional view of the adjustable valve unit of FIG. 3 along lines 4-4;

FIG. 8 is a cross-sectional view of the adjustable valve unit of FIG. 7 showing the transition to a different pressure setting;

FIG. 9 is a perspective view of the spring arm unit with optional torsion spring;

FIG. 9A is a top plan view of the element of FIG. 9;

FIG. 10 is a side cross-sectional view of the adjustable valve unit of FIG. 8 along lines 10-10 showing axial lifting of the rotatable construct;

FIG. 11 is a shallower partial top cross-sectional view of the adjustable valve unit of FIG. 6H showing the "virtual off" position in an unconstrained condition;

FIG. 12 is a side view along lines 12-12 of FIG. 11;

FIG. 13A is a partial cross-sectional view along lines 13A-13A of FIG. 13;

DETAILED DESCRIPTION OF THE INVENTION

Figure 1:
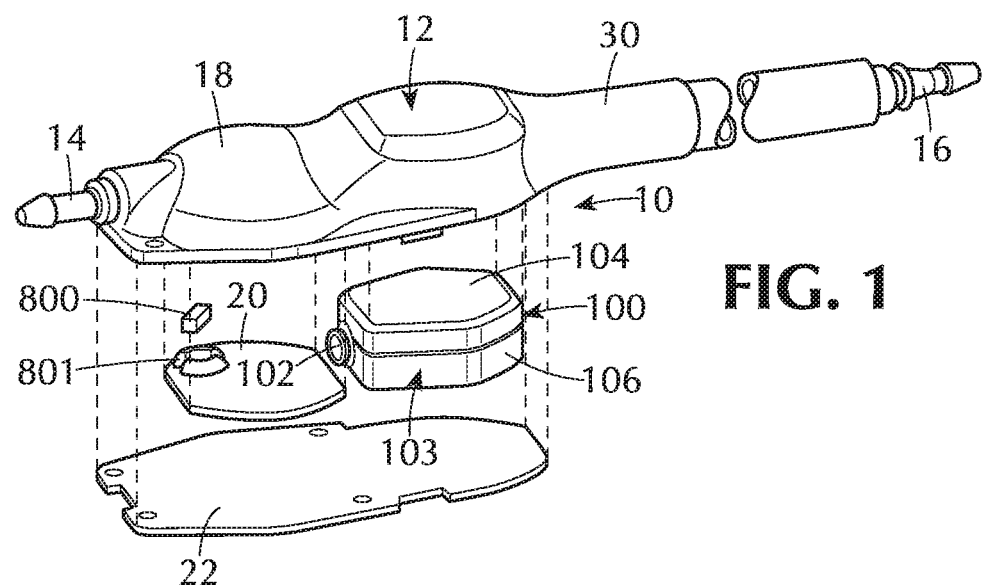
FIG. 1 is a schematic perspective exploded view of a programmable valve device having an adjustable valve unit.

FIG. 1 illustrates a prior art programmable shunt valve device 10 having a shunt housing 12, preferably formed of a translucent material such as silicone, with proximal connector 14 and distal connector 16. A ventricular catheter or other proximal catheter is connectable to connector 14 to bring fluid into shunt housing 12. Fluid passes into sampling or pumping chamber 18 and then through a valve mechanism in inlet 102 into adjustable valve unit 100, which is shown and described in more detail below in relation to FIGS. 2-13A. Valve unit 100, FIG. 1, includes a casing 103 formed as upper casing 104 and lower casing 106 which are joined by ultrasonic welding in this construction. A needle guard 20, preferably formed of a rigid polymeric material, and lower casing 106 are secured within housing 12 by a backing plate 22, preferably formed of silicone reinforced with a polymeric mesh, which is bonded to housing 12 by a medical grade epoxy. A fixed reference magnet 800, as described in detail further below, is preferably seated in a bump, cavity, pocket or projection 801 on the needle guard 20.

When fluid pressure at inlet 102 exceeds a selected pressure setting within valve unit 100, fluid is admitted past a valve mechanism and then flows through valve unit outlet 110 into passage 30 of housing 12. Ultimately, fluid exits from housing 12 through distal connector 16 into a peritoneal catheter or other distal catheter.

Figure 2:
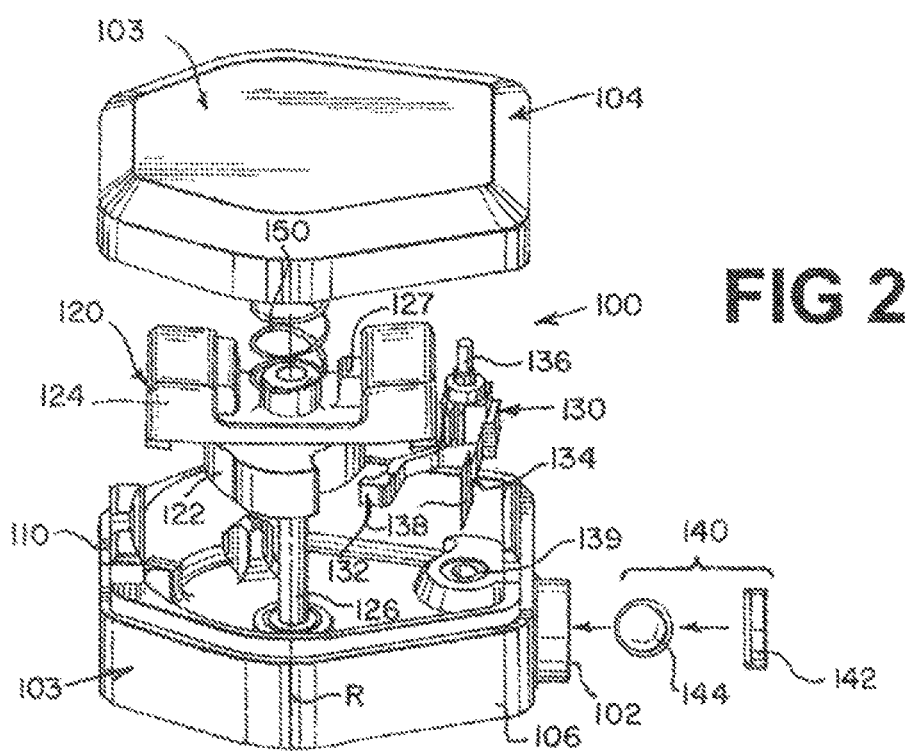
FIG. 2 is an exploded perspective view of the adjustable valve unit of FIG. 1.

Valve unit 100, FIG. 2, includes a rotor 120, spring arm unit 130, valve mechanism 140, and a rotor retention spring 150. Rotor 120, also referred to as a rotating construct, is formed of a lower cam structure 122 having a plurality of radially flat cam surfaces, as shown and described in more detail below, and an upper, magnet housing 124 carrying magnetic elements 123 and 125, N and S pole magnets, respectively. Housing 124 also defines a finger 127 which engages a stop in upper casing 104 when rotor 120 is moved to an unconstrained condition as described below. Rotor 120 rotates about axle 126 which defines a substantially fixed axis of rotation R at a first location in casing 103.

Preferably, rotor 120 is also capable of moving along the axis of rotation, in a translational motion, to an unconstrained condition when an adjuster tool is applied to it, as described in more detail below. Retention spring 150 biases rotor 120 to a downward, normally constrained condition. Preferably, spring 150 is a coil spring having sufficient bias to resist the effect of gravity, regardless of the position of the valve unit, and to resist magnetic or ferrous objects, such as magnets in an indicator tool described in more detail below. However, spring 150 is insufficient to resist the effects of an adjustment tool, also described below. Lower cam section 122 has a sufficient height to ensure that cam follower 132 remains in contact with a cam surface in both the constrained and unconstrained conditions.

Spring arm unit 130 includes cam follower 132, a resilient spring element 134, and upper and lower axles 136 and 138 at a second location in casing 103. Axle 138 turns about a bearing 139 formed of a low-friction, hard material such as synthetic ruby. It is desirable for casing 103, rotor 120 and spring arm unit 130 to be formed of polyethersulfone, while all spring components are formed of medical grade non-ferromagnetic stainless steel.

Valve mechanism 140 includes seat 142 and movable valve member 144. Preferably, seat 142 and valve member 144, such as a ball, are formed of the same non-ferromagnetic material such as synthetic ruby. In other constructions, the movable valve member may be a disc, a cone, or other type of plug. A spherical ball is currently preferred because that shape enables tight, precise tolerances, assembly and control relative to the valve seat. Also, the position of the seat within a port can be adjusted during assembly of the valve unit to alter the actual performance value achieved at each setting, using a force versus displacement relationship. First, a mandrel checks the position of the ball, and the seat is inserted to an estimated desirable location within the port. Ball displacement is tested at one or more settings to confirm that desired performance will be achieved.

Figure 5:
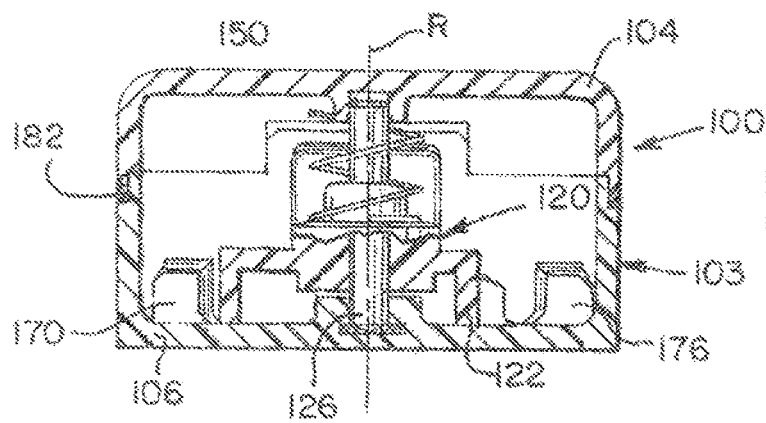
FIG. 5 is a cross-sectional view of the adjustable valve unit of FIG. 3 along lines 5-5.

Valve unit 100 is shown assembled in FIGS. 3-5 and positioned at a second pressure setting, as described in more detail below. Rotor housing 124 carries downwardly projecting teeth 160 and 162 with cooperate with four lock stops projecting upwardly from lower casing 106 in this construction. Lock stop 172 is shown in partial cross-section in FIG. 4 and lock stops 170 and 176 are visible in FIG. 5. Preferably, the lower surfaces of rotor teeth 160 and 162 are rounded and the upper surfaces of casing lock stops 170, 172, 174 and 176 each have a plurality of facets to create a chisel-like, lead-in topography which encourages the rotor teeth to return to a constrained position. However, the vertical surfaces of teeth 160, 162 and of stops 170-176 abut when engaged and do not "lead out", that is, relative translational movement is discouraged. Pure vertical lift must be provided by an adjustment tool, as described in more detail below, to overcome the tooth-to-stop abutment and change the performance setting.

A limiter 180, FIG. 4, restricts travel of spring 134 away from seat 142 so that ball 144 does not become misaligned or dislodged relative to seat 142. A gasket 182 of epoxy is shown in FIGS. 4 & 5 as an optional, redundant seal between upper casing 104 and lower casing 106 in this construction.

Figure 6:
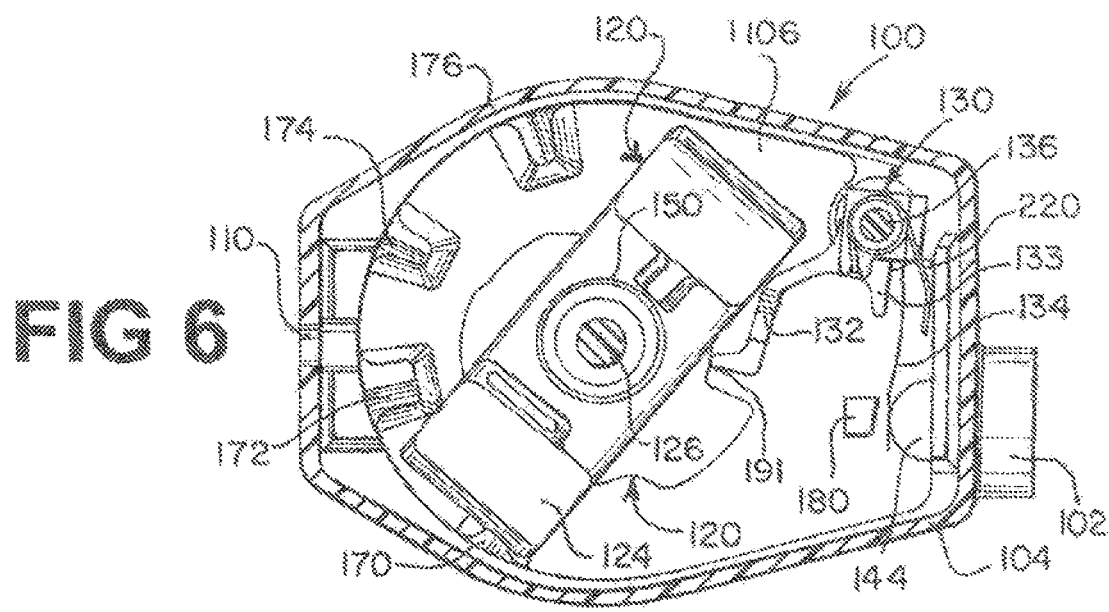
FIG. 6 is a partial cross-sectional view of the adjustable valve unit of FIG. 4 approximately along lines 6-6 at a first pressure setting.
Figure 6A:
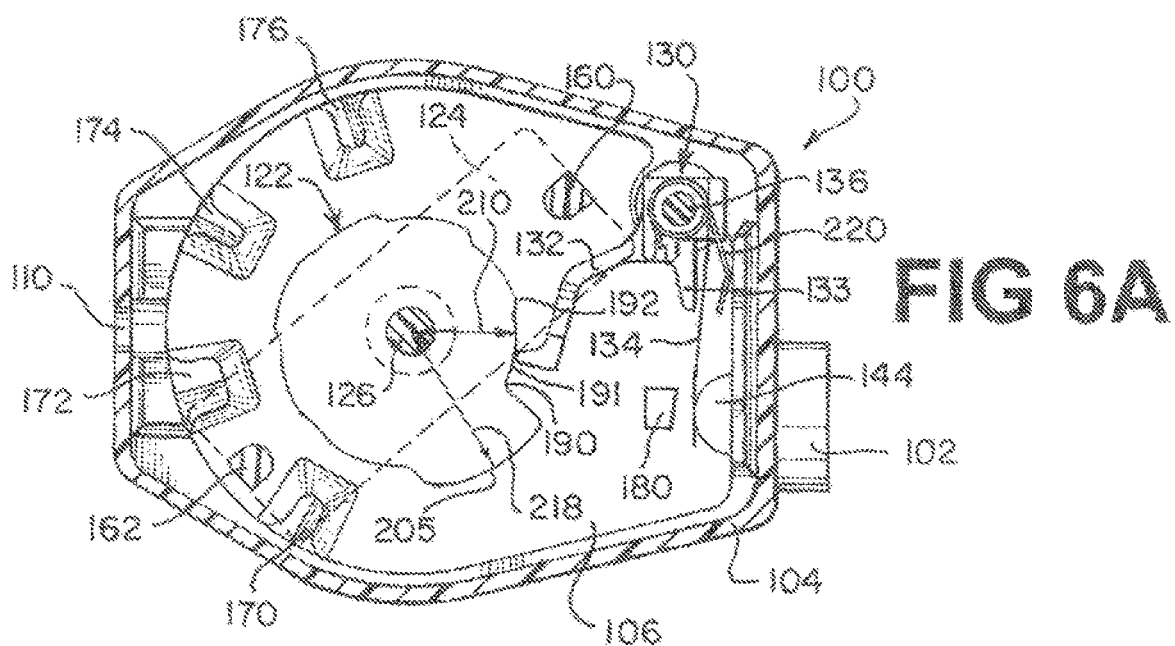
FIG. 6A is a deeper cross-sectional view of the adjustable valve unit of FIG. 4 approximately along lines 6A-6A at a first pressure setting.
Figure 7:
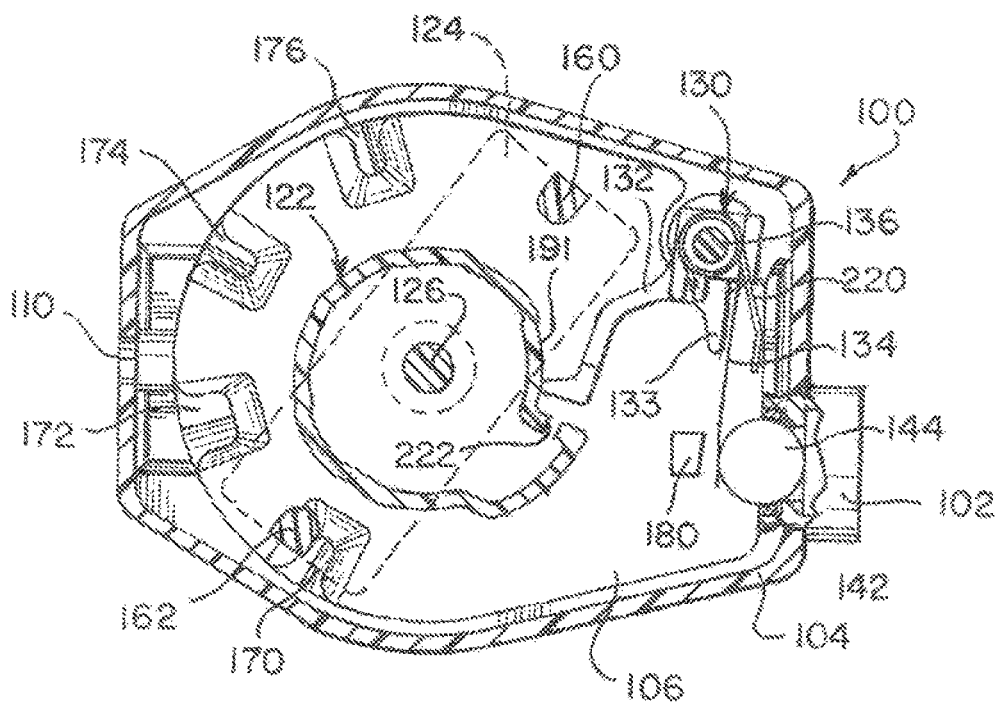
FIG. 7 is a deeper cross-sectional view of the adjustable valve unit of FIG. 4 approximately along lines 7-7.

The operation of valve unit 100 is illustrated in FIGS. 6-8 in relation to valve unit 100, with identical reference numerals identifying identical components and features. Not all such components and features are labelled in each drawing for the sake of visual clarity. FIGS. 6 & 6A show different levels of top partial cross-sectional views for valve unit 100 at a first pressure setting. Cam follower 132 slidably contacts only a first cam surface 191, which has an arc length bounded by points 190 and 192, because rotor housing tooth 162 is captured between casing lock stops 170 and 172 in the normal, constrained condition. First cam surface 191 has a first, preferably shortest radial distance 210 relative to the axis of rotation of rotor 120. By comparison, outermost cam surface 205 has a greatest radial distance 218. An optional torsion spring 220 is shown in greater detail in FIG. 9.

When rotor 120 is translated upwardly by magnets using an adjustment tool rotor tooth 162 is lifted so that subsequent clockwise or counter-clockwise rotation of the adjustment tool rotates tooth 162 up and over casing lock stop 172. After the adjustment tool is removed and when the second pressure setting has been selected as shown in FIG. 6B, rotor 120 is biased downwardly by spring 150, FIGS. 2, 4 & 5.

Figure 6B:
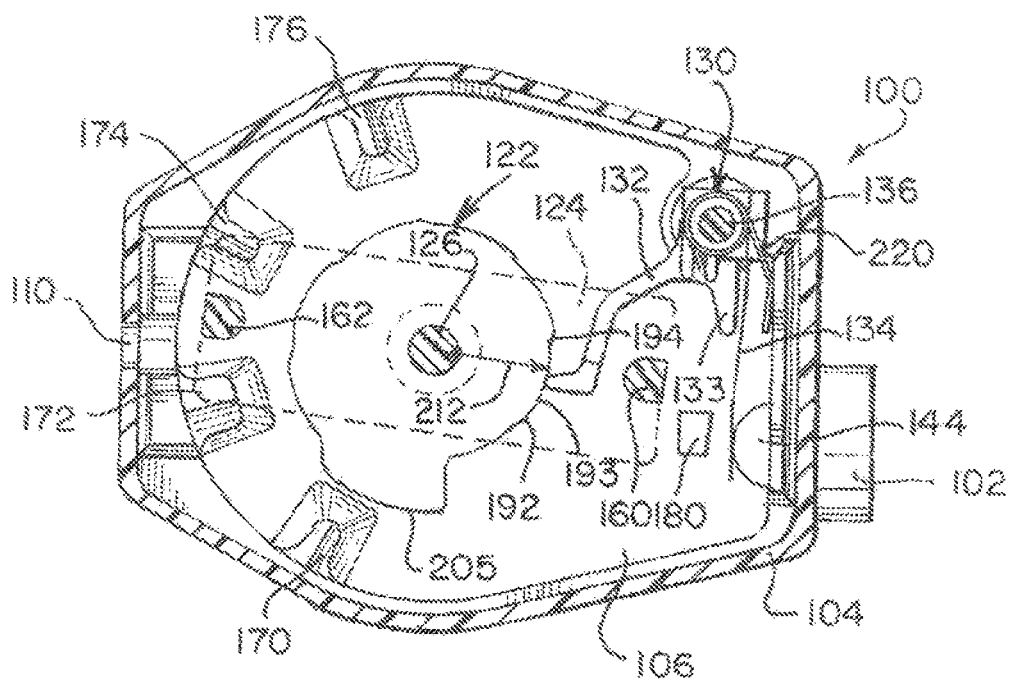
FIGS. 6B-6H are partial cross-sectional view of the adjustable valve unit of FIG. 4 at different, successive pressure settings.

Rotor tooth 160 is illustrated as not being in contact with any stop in FIGS. 4 & 6B, for example, because in the constrained condition rotor tooth 162 is now captured between a pair of lock stops 172 and 174, FIG. 6B, which is sufficient to prevent rotation of rotor 120 relative to the cam follower 132 beyond points 192 and 194 on the cam structure of rotor 120. Points 192 and 194 represent a second arc length for second cam surface 193. Surface 193 is at a second radial distance 212 which is greater than distance 210 and is less than distance 218, FIGS. 6A & 6H. The arc length of second cam surface 193, FIG. 6B, can be the same or different than the arc length of first cam surface 191 but, preferably, is substantially the same length.

The outward radial motion of cam follower 132 as it slidably travels from first cam surface 191, FIG. 6A, to second cam surface 193, FIG. 6B, increases the biasing force by valve spring 134 on ball 144 as increased torque is applied by cam follower 132 to the remainder of spring arm unit 130. Improved precision in pressure control is achieved by having a stiff cam follower 132 in contact with the selected cam surface and a flexible element, spring 134, in contact with the valve ball 144. The enhanced result is opening of the ball 144 from the valve seat 142 by requiring only the resilient spring element 134 to bend, which provides a constant spring force to the ball 144. The opening pressure, and overall valve performance, is not reliant on axial pivoting of the spring arm unit 130.

Figure 6C:
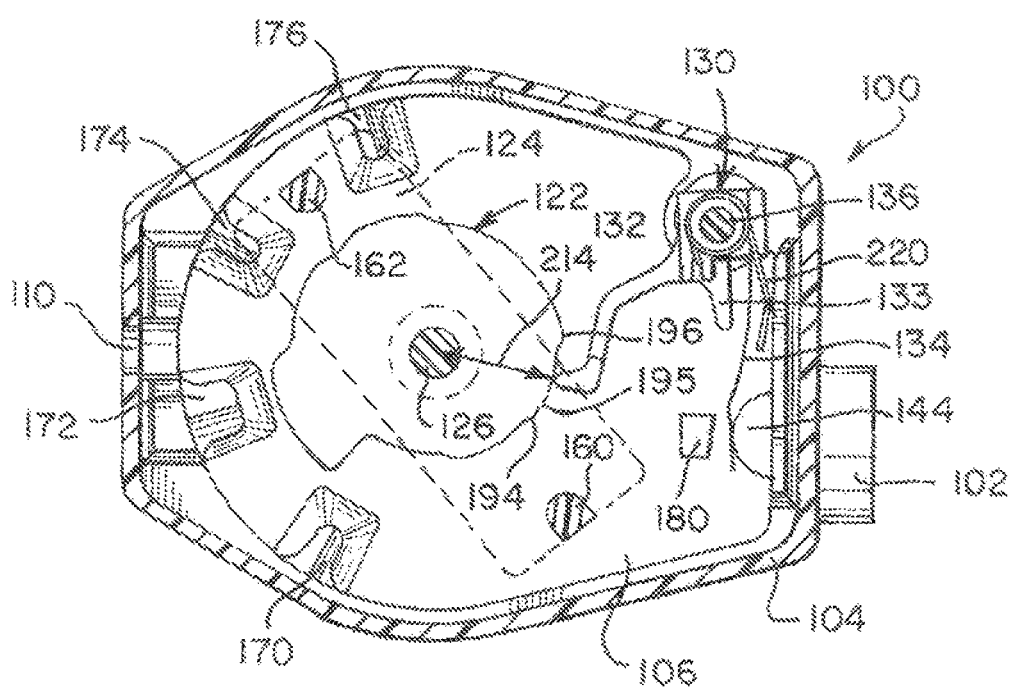
Figure 6D:
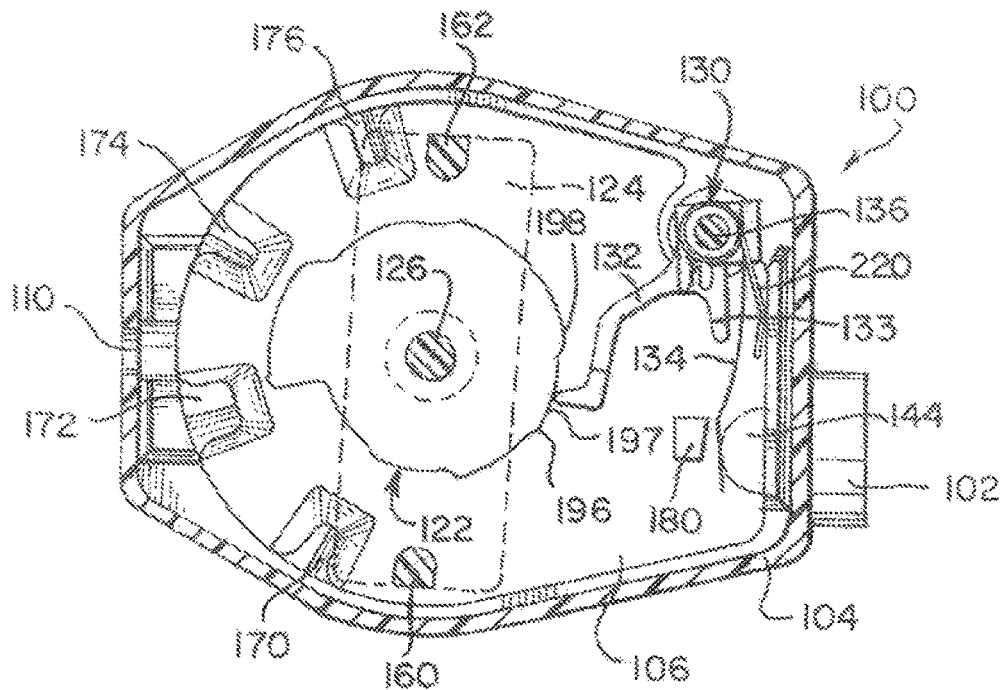

A third opening pressure setting is shown in FIG. 6C with rotor tooth 162 positioned between casing stops 174 and 176 such that cam follower 132 experiences only third cam surface 195 between points 194 and 196 at a third radial distance 214. To achieve a fourth pressure setting, FIG. 6D, both rotor teeth 160 and 162 are utilized relative to casing stops 170 and 176, respectively. Cam follower 132 is restricted thereby to fourth cam surface 197 between points 196 and 198.

Figure 6E:
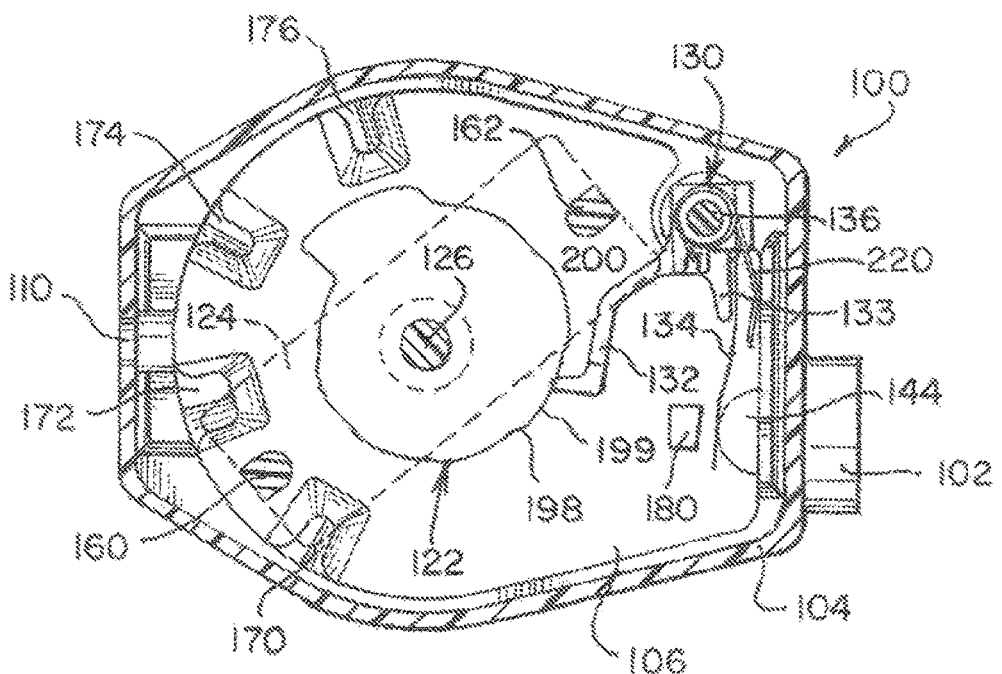
Figure 6F:
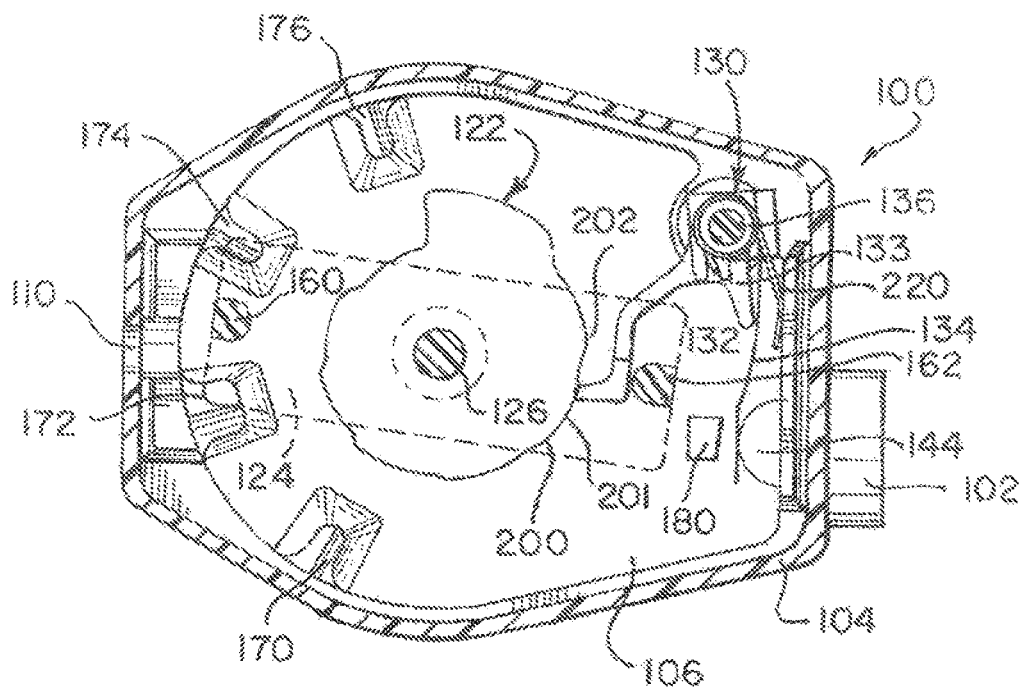
Figure 6G:
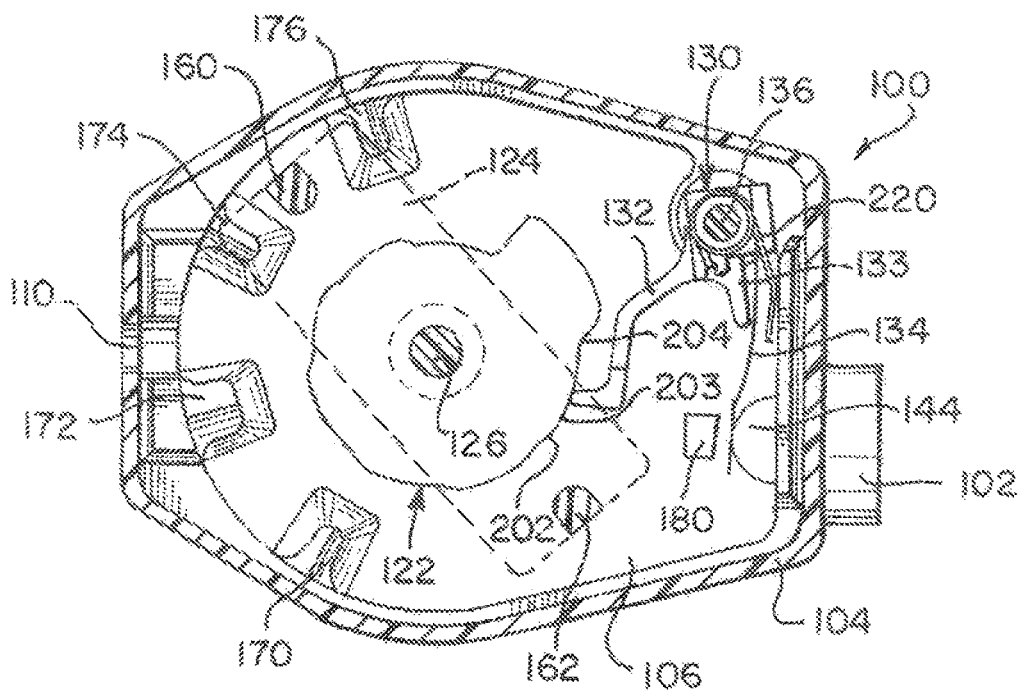

Fifth through seventh pressure settings are illustrated in FIGS. 6E-6G as rotor tooth 160 is successively captured between casing lock stop pairs 170-172, 172-174, and 174-176, respectively. Cam follower 132 is restricted thereby to fifth cam surface 199 between points 198 and 200, FIG. 6E, sixth cam surface 201 between points 200 and 202, FIG. 6F, and seventh cam surface 203 between points 202 and 204, FIG. 6G.

Preferred opening pressure settings currently range from approximately 30 mm to 210 mm water (294 Pa to 2,059 Pa) in seven increments of 30 mm (294 Pa), with a final, "virtual off" setting described in more detail below. Preferably, each valve unit is calibrated and tested at the time of manufacture at one or more flow rates. Actual opening pressure for each setting tends to vary according to flow rate, typically measured in milliliters per hour. Also, when tested with a 120 cm long distal catheter having an inner diameter of 1 mm, the average opening pressure typically will increase by 9 mm water or more at flow rates of 5 ml/h or more.

Figure 6H:
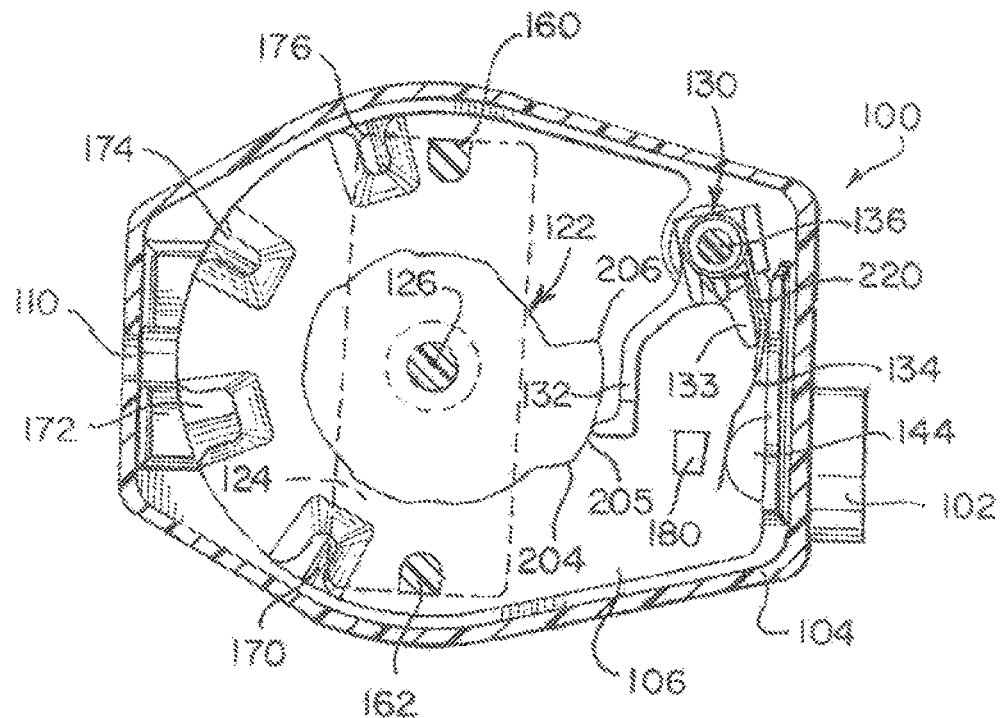

The final setting, FIG. 6H, of approximately at least 400 mm water (3,920 Pa) minimizes flow as a "virtual off" setting, that is, as substantially closed. This final setting is achieved by exposing cam follower 132 to outermost cam surface 205, defined by points 204 and 206, having greatest radial distance 218. This greatest cam setting forces stiffener element 133 of spring arm unit 130 against valve spring 134 to shorten its active, effective length and thereby dramatically increase the biasing force applied against ball 144. The final opening pressure is increased by more than fifty percent over the prior setting. In other constructions, a stiffener element is forced against a valve spring during two or more final cam settings at desired pressure increments.

Spring arm unit 130 is shown in greater detail in FIGS. 9 and 9A with cam follower 132, stiffener element 133, and valve spring 134. Cam follower 132 terminates in a triangular head 233 with rounded or chamfered edges, one of which serves as a bearing surface 235. In a preferred construction, spring element 134 is formed from stainless steel having a thickness of 0.020 inches and terminates in an enlarged pad 230 for contacting the valve ball or other movable valve member. In one construction, spring element 134 is attached to the remainder of spring arm unit 130 by a post 232 and rivet 234 which are secured by ultrasonic welding. Torsion spring 220 has a first leg 221 which is retained in recess 236 of projection 238. Second spring leg 223 rests against an inner surface of the casing.

Use of torsion spring 220 is optional, and is possible because only spring element 134 contacts the movable valve member. As a result, additional spring force from torsion spring 220 can be utilized to force bearing surface 235 of cam follower 132 against a cam surface of the rotor. This biasing force provided by torsion spring 220 augments rotational position of the spring arm reflective of the intended cam displacement without otherwise impacting the force applied to the ball or other movable valve member. This provides for a more accurate and repeatable opening pressure and a more manufacturable and robust design as it reduces the need to maintain minimal friction such as when the valve spring element solely provides the force needed to maintain the cam follower on the cam surface.

The position of the components and features within valve unit 100 at the first pressure setting shown in FIG. 6A is illustrated at a deeper partial cross-sectional view in FIG. 7. Opening 222 into the lower cam portion of rotor 120 inhibits negative pressure from developing under rotor 120, that is, opening 222 ensures pressure equalization as cerebrospinal fluid passes through valve unit 100.

The transition from the first pressure setting to the second pressure setting is illustrated in FIGS. 8 & 10 as rotor 120 is translated upwardly by magnetic attraction with an adjustment tool so that rotor tooth 162 is able to clear casing lock stop 172. Cam follower 132 is shown in FIG. 8 at point 192 passing from first cam surface 191 to second cam surface 193. Lower cam section 122 has a sufficient height relative to cam follower bearing surface 235 to ensure that cam follower 132 remains in contact with a cam surface of cam portion 122 in both the constrained and unconstrained conditions. Rotor retention spring 150, FIG. 10, has been compressed, its biasing force being overcome by magnetic attraction between rotor 120 and the adjustment tool while it is positioned over valve unit 100. Also illustrated in FIG. 10 are upper and lower synthetic ruby bearings 242 and 139 for upper and lower axles 136 and 138, respectively, of spring arm unit 130. Synthetic ruby bearing 240 rotatably supports rotor axle 126.

The position of the components and features within valve unit 100 at the final, "virtual off" or substantially closed setting shown in FIG. 6H is depicted at a shallower cross-sectional view in FIG. 11 in an unconstrained condition. Further clockwise rotation of rotor 120 is prevented by rotation stop or limiter 250 which projects downwardly from upper casing 104 to contact finger 127. Rotation stop 250 contacts the opposite surface of finger 127 when rotor 120 is turned fully counter-clockwise in an unconstrained condition. The actual position of rotation stop 250 may be shifted to the right of the position shown in FIG. 11 so that cam follower 132 is able to track nearly the entire portion of cam surface 205. Preferably, one side of stop 250 prevents rotor movement from the lowest setting directly to the highest setting, and also prevents the cam follower from touching the cam projection for the highest setting when the rotor is at its lowest setting. The other side of stop 250 prevents movement from the highest setting directly to the lowest setting. A side, partial cross-sectional view of rotation stop 250 blocking rotor housing 124, as well as spring 150 compressed between rotor 120 and upper casing 104, is shown in FIG. 12 for this unconstrained condition.

Figure 13:
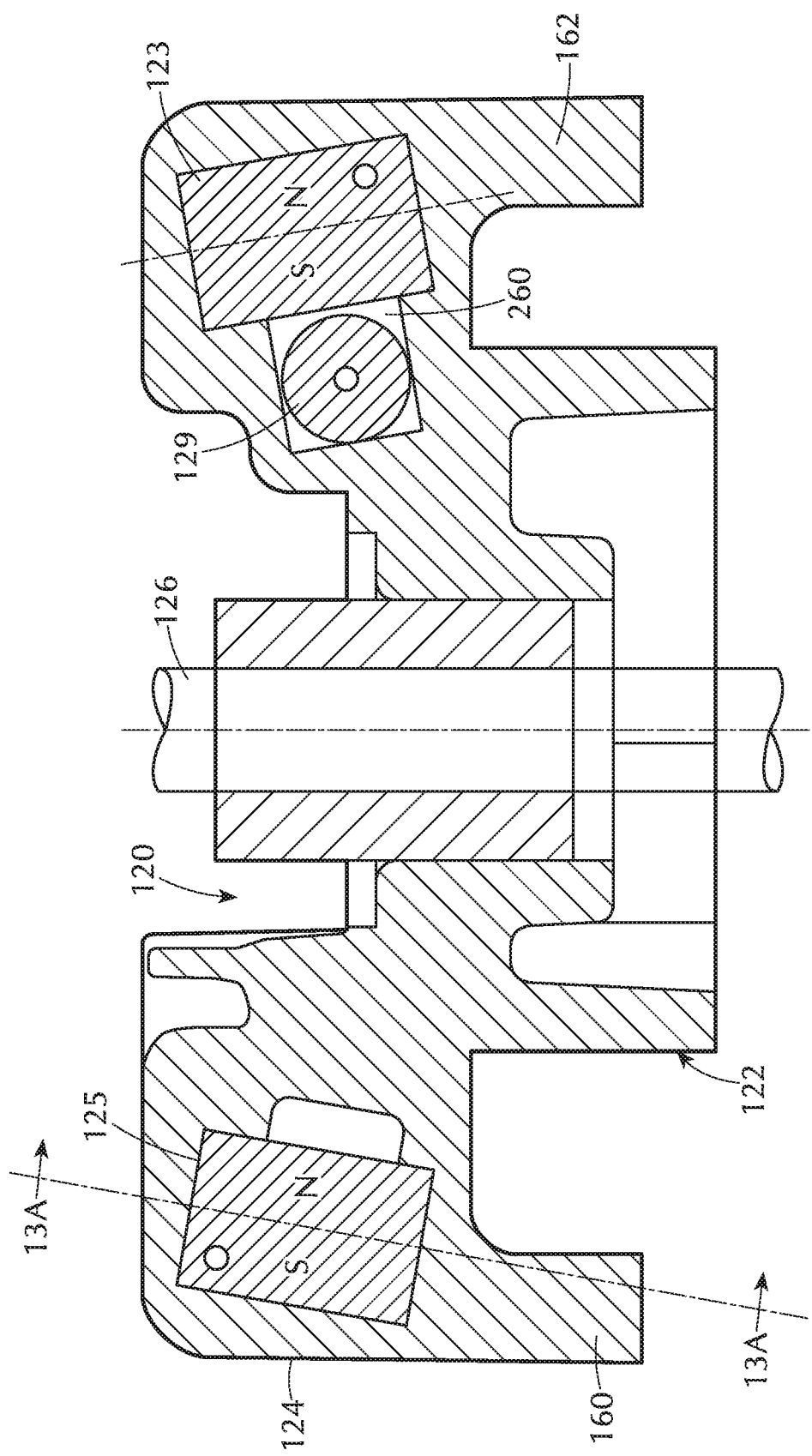
FIG. 13 is a side cross-sectional view along lines 13-13 of FIG. 11.

Further detailed views of selected features and components of rotor 120 in one construction are illustrated in FIGS. 13 & 13A. In particular, the housing portion 124 is shown as integral with cam portion 122, similar to monolithic rotor 120a of FIG. 1A. Pocket cavity 260, FIG. 13, contains magnet 123 and tantalum reference ball 129 which is readily visible during imaging of the valve unit 100 after implantation in a patient to confirm the actual pressure setting. Pocket cavity 262 holds magnet 125. A partial end view of housing portion 124 through magnet 125, pocket 262 and rotor tooth 160 is provided in FIG. 13A.

Figure 14:
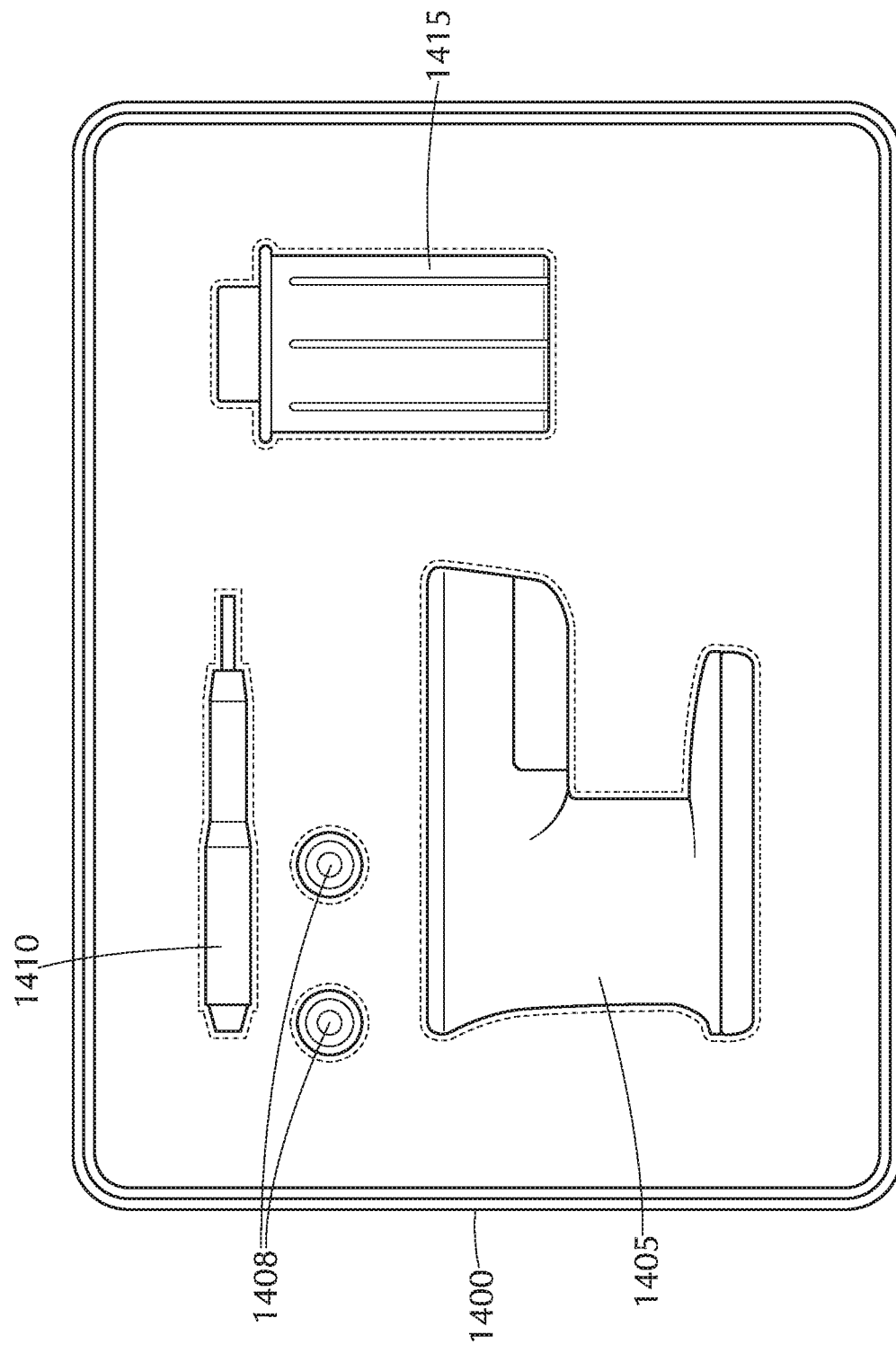
FIG. 14 is a perspective view of an electronic tool set including an integrated locator/indicator tool, an adjustment tool and a screwdriver in accordance with the present invention.
Figure 14A:
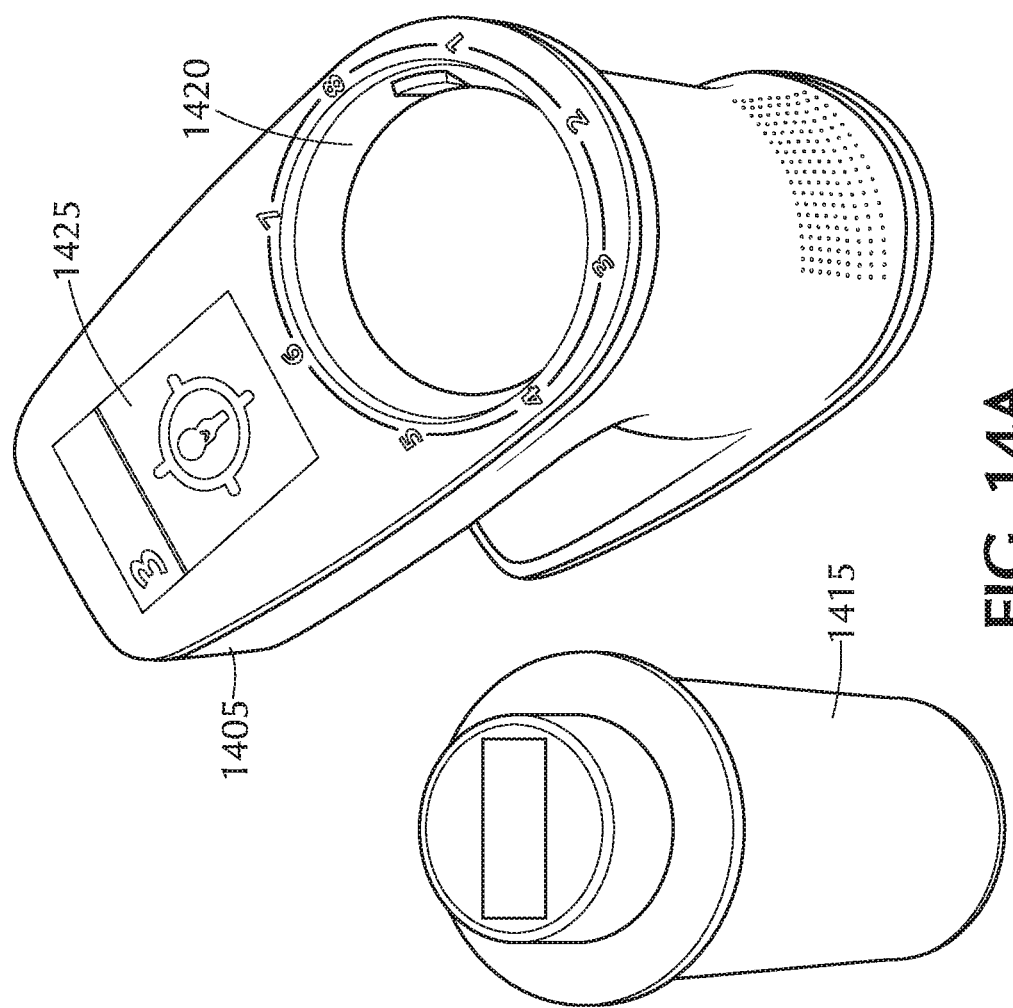
FIG. 14A is a top perspective view of the integrated locator/indicator tool and adjustment tool of FIG. 14, prior to the adjustment tool being inserted into the integrated locator/indicator tool.
Figure 14B:
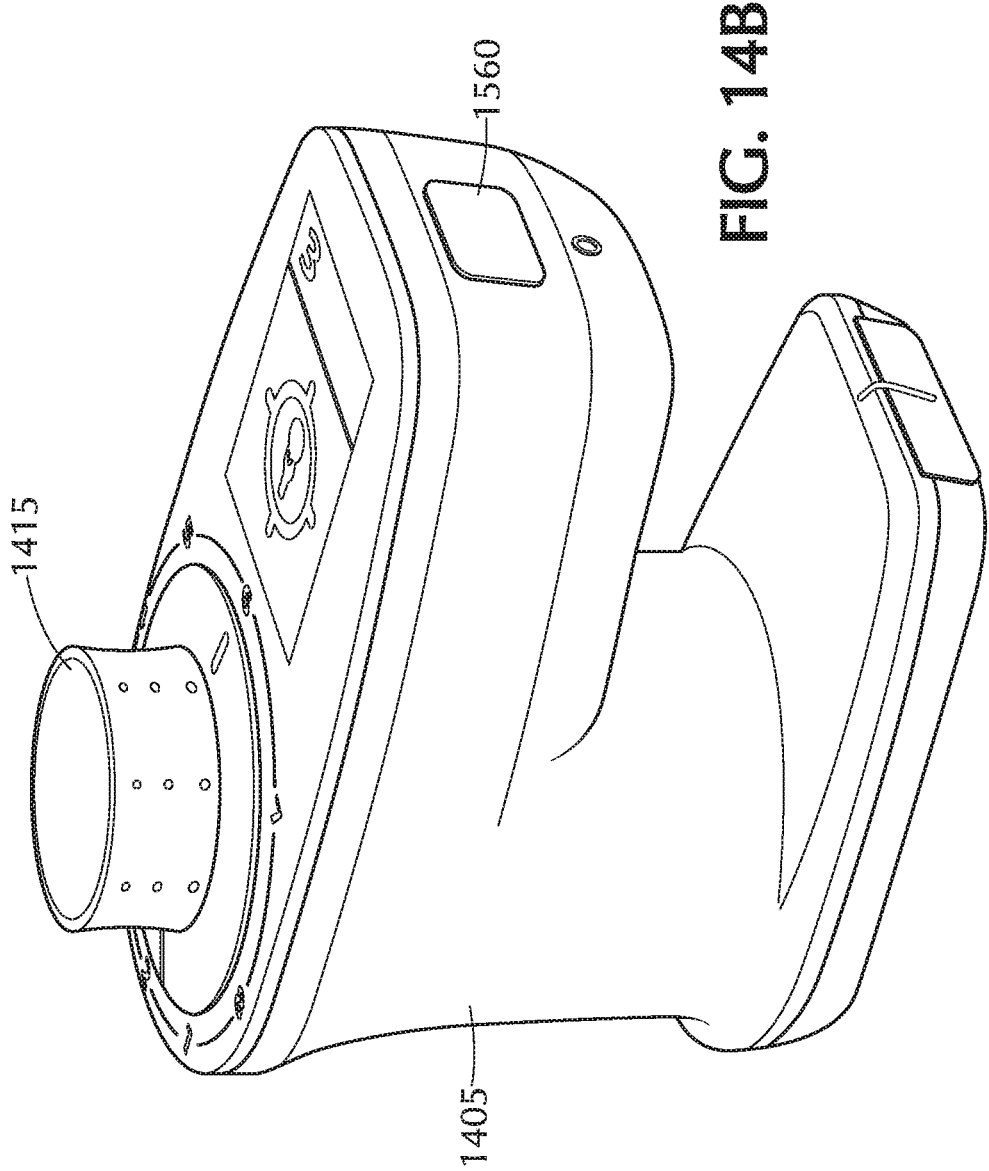
FIG. 14B is a top perspective view of the integrated locator/indicator tool and adjustment tool of FIG. 14, with the adjustment tool inserted into a complementary cavity in the integrated locator/indicator tool.

FIG. 14 is a perspective view of a present inventive electronic tool 1400 set stored in a case wherein the toolset includes an integrated locator/indicator tool 1405, an adjustment tool 1415 and a screwdriver 1410. The toolset in FIG. 14 includes an integrated locator/indicator tool 1405, however, the present invention is also applicable for toolsets in which none, some or all of the tools are integrated into a single device. A top perspective view of the integrated locator/indicator tool 1405 and adjustment tool 1415 of FIG. 14, prior to the adjustment tool 1415 being inserted into a cavity 1420 of the integrated locator/indicator tool 1405, is shown in FIG. 14A. While FIG. 14B shows the adjustment tool 1415 following insertion into the cavity 1420.

Figure 15:
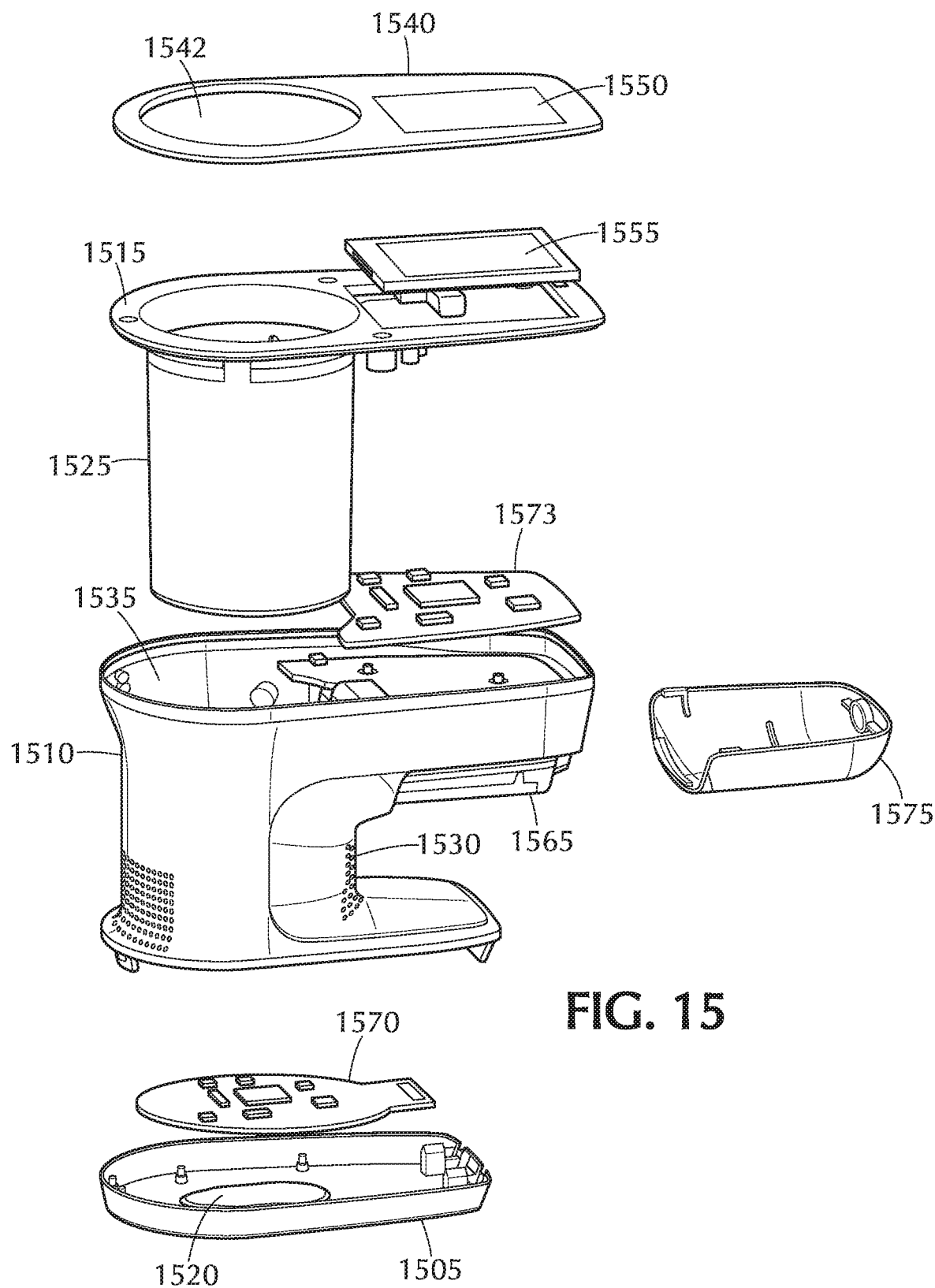
FIG. 15 is an exploded view of the integrated locator/indicator tool of FIG. 14.

FIG. 15 is an exploded perspective view of the integrated locator/indicator tool 1405 of FIG. 14 which includes a housing 1500. In the illustrated example, housing 1500 comprises a bottom housing section 1505, a middle housing section 1510 and a top housing section 1515, each separate from one another. A cylindrical shaped section 1530 of the middle housing section 1510 defines a passageway or channel 1535 extending longitudinally therethrough. Top housing section 1515 has a chimney 1525 complementary in size and shape to be received within the passageway or channel 1535 of the cylindrical shaped section 1530 of the middle housing section 1510. Chimney 1525 is closed at one end and open at an opposite end. The open end of the chimney 1525 receiving therein the adjustment tool 1415, as described in detail below. An exterior surface of the bottom housing section 1505 has a recess 1520 defined therein that is complementary in shape and size to the outer contour of the programmable implantable bodily fluid drainage valve. In use, the integrated location/indication tool 1405 is positioned with the exterior surface of the bottom housing section 1505 against the skin of the patient and the implantable bodily fluid drainage valve seated within the recess 1520. A top covering or layer 1540 may be mounted to the top of the assembled housing. Such covering or layer 1540 has a complementary size and shape opening 1542 to that of the chimney 1525. Disposed about the perimeter of the opening 1542 are a series of markings representing the different valve settings in predetermined increments (e.g., 1, 2, 3, 6, 7, 8). A second opening 1550 in the top covering or layer 1540 permits viewing therethrough of a display 1555, such as a Liquid Crystal Display (LCD). The integrated locator/indicator tool 1405 is powered by one or more batteries and turned ON/OFF by a button 1560. The batteries are housed within a battery enclosure assembly 1565 that includes a tray with electronic contact terminals between which the batteries are inserted. Access to the battery enclosure assembly 1565 for insertion/removal of the batteries therefrom is via a removable battery door assembly 1575. A two-dimensional array of 3-axis magneto-resistive sensors 1570 printed on a circuit board detects the magnetic field pattern produced by the magnetic elements 123, 125 disposed in the housing 124 of the rotor 120 and the fixed reference magnet 800. It is within the intended scope of the present invention to substitute other types of sensor arrays capable of detecting magnetic fields, such as Hall sensors, for the 3-axis magneto-resistive sensors 1570. Printed circuit board 1573 includes controller circuitry for controlling the integrated locator/indicator tool 1405. In contrast to conventional toolsets, the integrated locator/indicator tool 1405 of the present inventive toolset 1400 does not have any openings through which the user is able to manually palpate the valve. Instead, all feedback for locating the valve center and orientation angle is given electronically on the display 1555. This configuration (without the need for an opening or hole in the middle of the sensor array through which the user palpates the valve) is advantageous in protecting against 'closed' sensor arrays. If such an opening or hole in the middle of the sensor array were required the present inventive sensor array configuration would have been significantly more complex, if not impossible.

Figure 16:
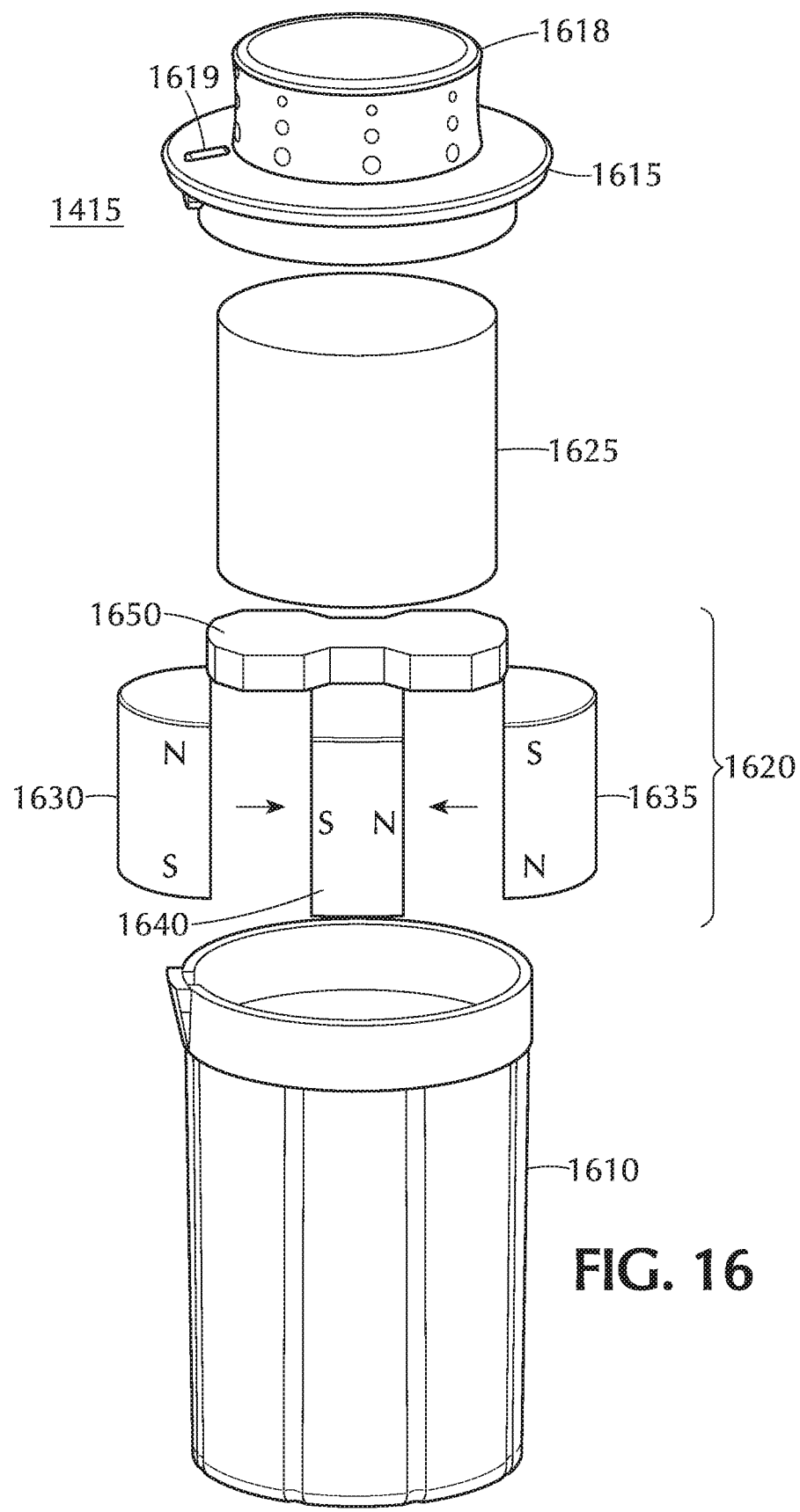
FIG. 16 is an exploded view of the adjustment tool of FIG. 14.
Figure 16A:
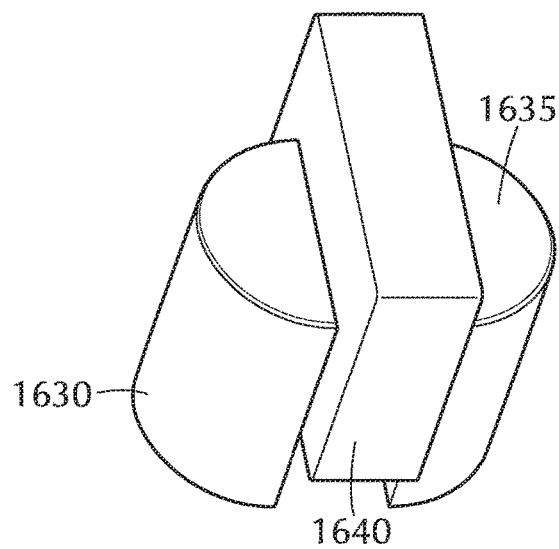
FIG. 16A is a perspective view of the placement of the half round magnets on either side of the shield magnet comprising part of the magnet assembly of FIG. 14.
Figure 16B:
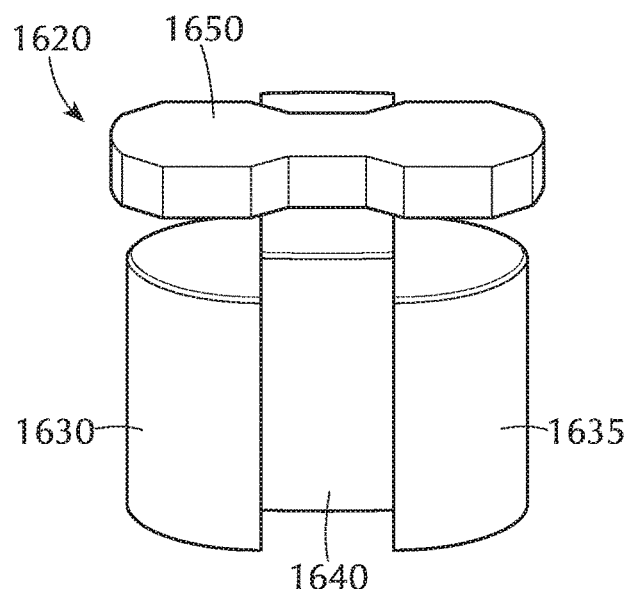
FIG. 16B is a perspective view of the assembled magnet assembly of FIG. 14.
Figure 16C:
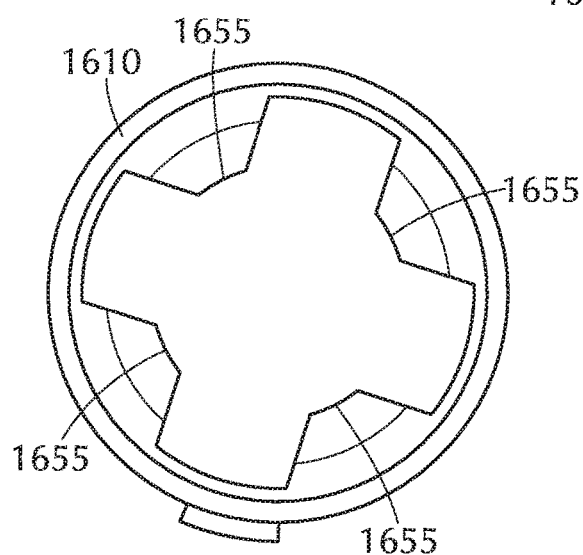
FIG. 16C is a top view of the assembled bottom and middle housing sections of the adjustment tool of FIG. 14 showing the internal vertical ribs.
Figure 16D:
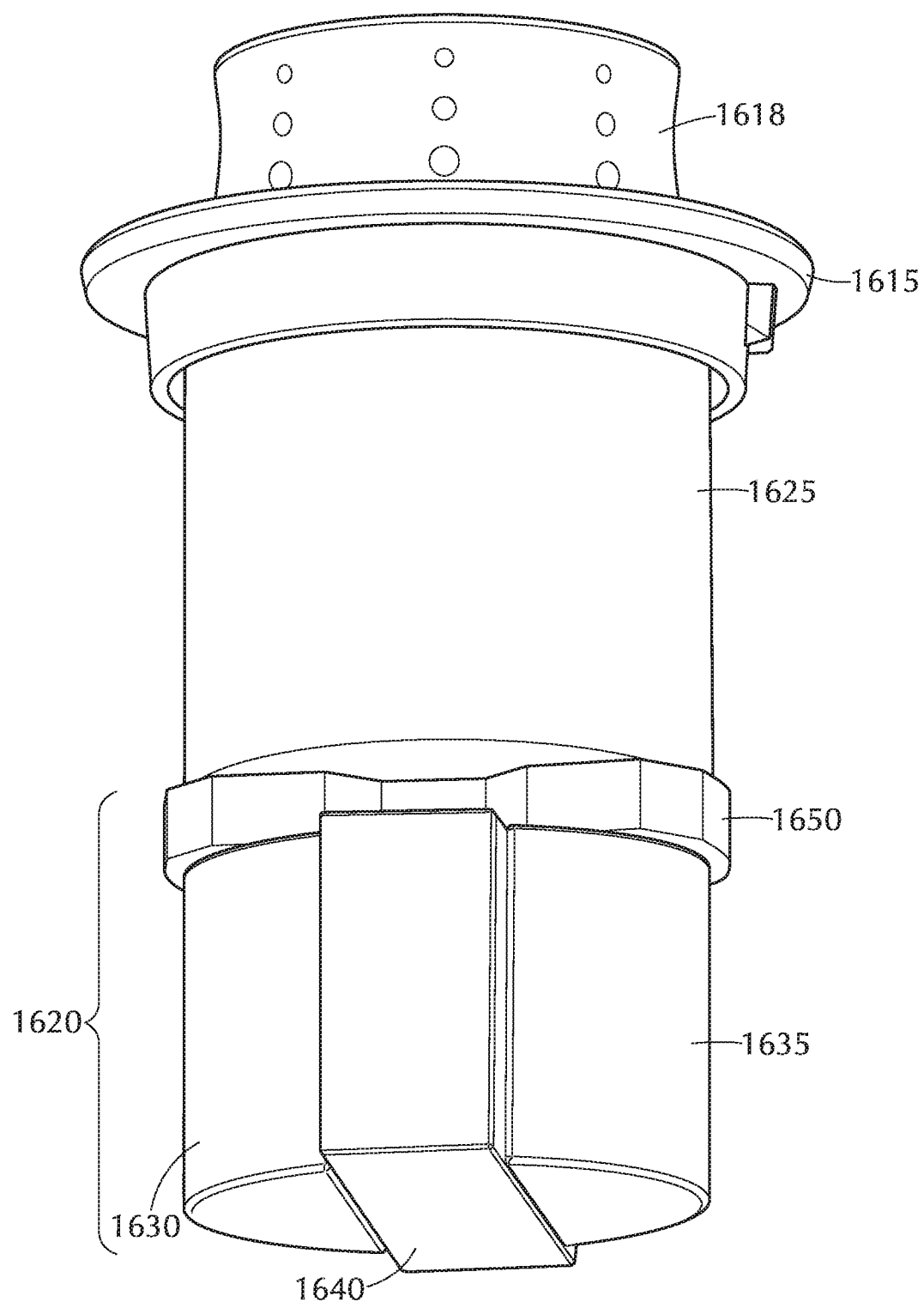
FIG. 16D is a perspective view of the assembled adjustment tool of FIG. 14 without the outer housing section to illustrate the magnet assembly.

FIG. 16 is an exploded perspective view of the adjustment tool 1415 of FIG. 14. In the illustrated example, housing 1600 comprises an outer housing section 1610 and a top housing section 1615, each separate from one another. A magnet assembly 1620 is disposed in the outer housing section 1610. In particular, the magnet assembly 1620 in FIG. 16A is a Halbach array comprising two half round magnets 1630, 1635 connected by a yoke 1650 and separated by a shield magnet 1640 that redirects the magnetic field allowing deeper penetration. The strength of the half round magnets 1630, 1635 selected for use in the adjustment tool 1415 depends on one or more factors, such as distance from the valve and the design of the sensor array. In the magnet assembly 1620, the two half round magnets 1630, 1635 are rotated until their flat side lays flush against the shield magnet 1640, as depicted in FIGS. 16, 16A, 16B & 16D. The orientation of the magnets 1640, 1630, 1635 should preferably with the magnet north side of the shield magnet 1640 in contact with the half round magnet 1630, 1635 with a magnetic north pointed toward the bottom of the outer housing section 1610. One of the two half round magnets 1630, 1635 faces the tantalum reference ball 129 (FIG. 13). The shield magnet 1640 is partially repelled by the half round magnets 130, 1635 and thus is held down by a yoke 1650 mounted on top of the shield magnet 1640 that, when assembled, is also in contact with the two half round magnets 1630, 1635. It is these components of the magnet assembly 1620 that when assembled together are inserted into the outer housing section 1610 so that the two half round magnets 1630, 1635 are received in respective recesses defined in an interior surface of the outer housing section 1610 with the half round magnet facing the tantalum ball 129 facing towards the '1 to 8 stop'. As is visible in the top view in FIG. 16C, the outer housing section 1610 includes a plurality of vertical ribs 1655 with which the half round magnets 1630, 1635 connect. A cylindrical shaped spacer 1625 is positioned above the yoke 1650 (FIG. 16D). The top housing section 1615 with a marking indicator is secured to the outer housing section 1610 forming the assembled adjustment tool 1415.

The half round magnets 1630, 1635 in the adjustment tool for changing or adjusting the valve setting are relatively strong magnets sufficient to rotate the magnets 123, 125 associated with the rotation construct 120 in the adjustable valve unit 100 to a desired valve setting. These magnets 1630, 1635 may overload the magneto-resistive sensor array 1570 in the locator/indicator tool 1405 after insertion of the adjustment tool 1415. In addition, the magnets 1630, 1635 in the adjustment tool 1415 may induce magnetic fields in ferromagnetic system components (e.g., batteries) of the locator/indicator tool 1405 leaving remanence or remnant magnetization (i.e., residual magnetism left behind in a ferromagnetic material such as iron) after the external magnetic field is removed (after the adjuster tool is removed following programming of the valve). The residual magnetism in the batteries of the locator/indicator tool 1405 may undesirably influence the magneto-resistive sensor array 1570 resulting in improper detection of the valve magnets 123, 125 and fixed reference magnet 800 in the adjustable valve unit 100. Heretofore, to compensate for such undesirable influence of the magnetic fields produced by the magnets 1630, 1635 in the adjustment tool 1415, following adjustment of the valve setting, the adjustment tool 1415 had to be removed and the indicator tool 1405 moved away a sufficient distance from the valve in order to recalibrate, clear or zero out the indicator tool 1405. After being recalibrated, once again the location of the center of the valve had to be found with the locator tool 1405 and then the indication or valve setting had to be read to be confirmed. Of course, if the valve setting had in fact changed (i.e., been altered by the magnetic fields produced by the magnets 1630, 1635 associated with the adjustment tool 1415) then the valve would have to be programmed to the correct valve setting using the adjustment tool 1415. These safety precaution measures often become redundant with the same steps having to be performed cyclically over-and-over again consuming medical personnel's valuable time and hence not always followed by the user, not to mention the increased probability of human error with each additional step that is required.

Current tool sets using analog compass systems do not require the user to recalibrate and relocate the valve after adjustment of the valve setting, which is one factor limiting adoption of programmable valve systems with associated electronic toolsets that do require recalibration before confirmation of the valve setting following adjustment. It is noted that the issue of overloading of the magneto-resistive sensor array 1570 may be avoided by selection of the proper sensors that do not need to be reset after being overloaded with the adjustment tool. For example, sensors having a resolution <approximately 0.5 μT, are resistant to perming, and thus can be exposed to magnetic fields associated with the adjustment tool without damaging the sensor. However, the other issue raised regarding inducing residual magnetization in system components (e.g., batteries) cannot be readily negated by merely selecting different system components. The reason being that non-ferromagnetic batteries are not readily available off-the-shelf for purchase. Customized batteries may be selected that are non-ferromagnetic to reduce the risk of residual magnetic field, however, the cost associated with such custom components is prohibitive. Another possible solution is to simply move those ferromagnetic system components (e.g., batteries) at risk of producing residual magnetic fields a greater distance away from the magneto-resistive sensor array. This solution is impractical due to the increase in size of the tools making it significantly more cumbersome to use.

The present invention has developed an improved toolset in which the ferromagnetic system components (e.g., batteries) in the integrated location/indication tool 1405 are fully or partially shielded from magnetic fields produced by magnets 1630, 1635 in the adjustment tool 1415 and magnetic field sensing components (e.g., sensor array 1570) are fully or partially shielded from the residual magnetic field in ferromagnetic system components (e.g., batteries) surrounded by the shield thereby eliminating the requirement to remove the location/indication tool 1405 from the patient for recalibrating, clearing or zeroing the sensors prior to confirming the valve performance setting after adjustment. Thus, the present inventive goal is to develop an improved electronic toolset that substantially reduces, if not prohibits, the retaining of magnetic charge by ferromagnetic system components (e.g., batteries) that otherwise would undesirably influence the sensor array resulting in an improper operation in detecting the center of the valve and/or reading of the valve setting and/or shielding magnetic field sensing components 1570 from the residual magnetic field in the ferromagnetic system components (e.g., batteries). This is realized by enclosing, encasing or covering the ferromagnetic system component(s) (e.g., batteries) in a magnetic shielding cage with a relatively very high permeability (permeability, $\mu_z \geq$ approximately $1.0 \times 10^{-4}$ @ peak flux density of 4 mT) such as a permalloy (containing approximately 80% nickel and approximately 20% iron content), in particular, MuMetal® grade ASTM A753 Alloy 4 a nickel-iron soft ferromagnetic alloy with very high permeability that varies by grade and thickness. Other magnetic shielding alloys may be used that have a very high magnetic susceptibility (e.g., saturation level of approximately 0.76 T) to an applied magnetic field so that it readily accepts the flow of magnetic field thereby redirecting the magnetic field lines away from areas desired to be substantially magnetic field free. Additional layers of shield may be applied with different levels of permeability/susceptibility depending on the frequency and strength of magnetic fields to be shielded. Intuitively a magnetic shielding alloy could be used to protect the sensor array to reduce the influence from external fields or effects of insertion of the adjustment tool. However, magnetic shielding cannot completely encase the sensor array or it would otherwise shield the magnetic fields of the implanted valve system; preventing the device from locating the implanted valve. Furthermore, encasing the sensor array in a magnetic shield would limit, or otherwise prohibit entirely, the magnetic field generated by the adjustment tool from intentionally penetrating to the implanted valve for adjustment of the valve setting. Therefore, limiting the magnetic shield to enclose only a portion of the sensor array necessary to maintain proper operation of the adjustment tool limits the effectiveness of the shielding thereby defeating its intended purpose. The present inventive configuration, however, is counterintuitive in approach in that it allows for temporary influence of the adjustment tool while inserted in the adjustment tool cavity, while preventing overloading of the sensor array that would otherwise make it possible to visualize the implanted valve magnets 123, 125, but significantly reduces or eliminates the propagation of a residual magnetic field from the shielded ferromagnetic system components (e.g., batteries). A constant magnetic field in proximity to the sensor array may be zeroed with a one time calibration or zeroing on startup. However, when inserting the adjustment tool 1415 into the adjustment tool cavity 1420 of the integrated locator/indicator tool 1405, the residual magnetic field in the batteries will change dynamically based on the magnetizing field of the adjustment tool magnets 1630, 1635, which changes based on the valve setting being programmed from/to.

Figure 17:
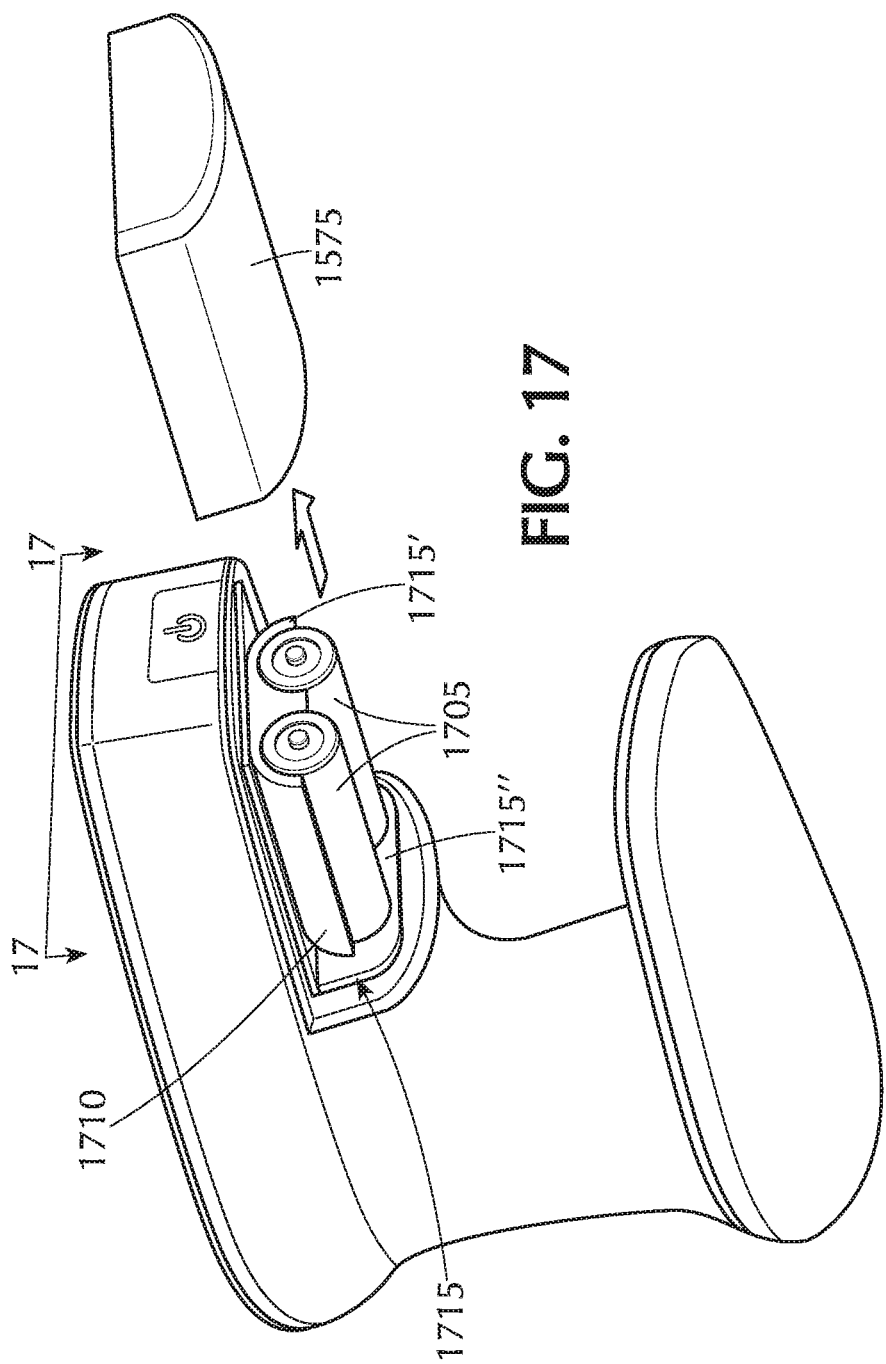
FIG. 17 is an exploded view of the battery door assembly from that of the assembled integrated locator/indicator tool of FIG. 14.
Figure 17A:
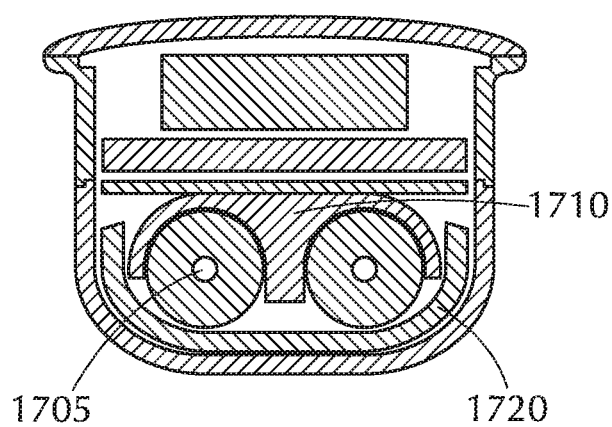
FIG. 17A is a cross-sectional view of the integrated locator/indicator tool of FIG. 17 along lines 17-17.
Figure 17B:
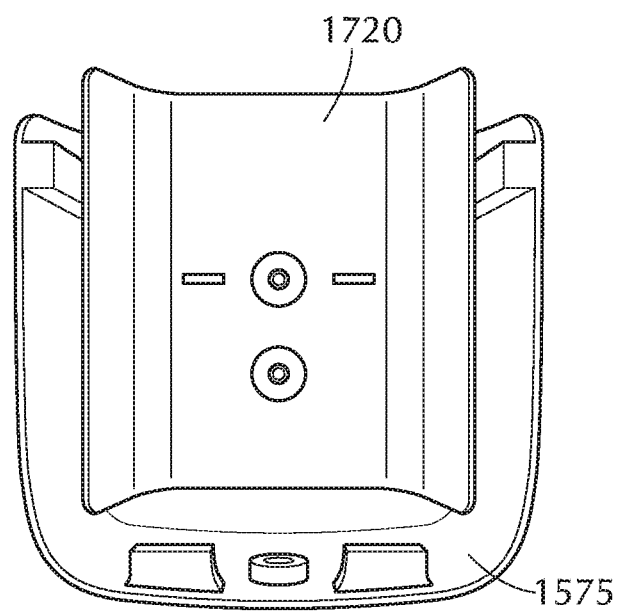
FIG. 17B is front view of the battery door assembly of the integrated locator/indicator tool.
Figure 17C:
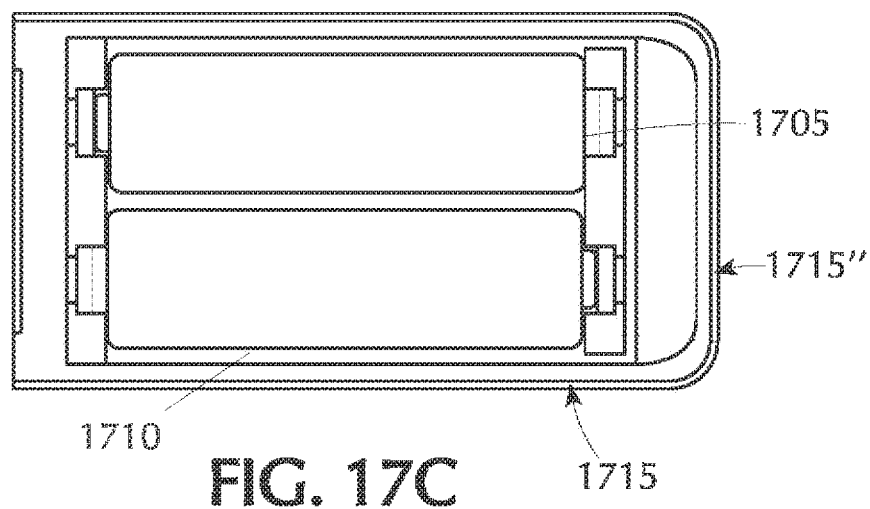
FIG. 17C is a top view of the battery tray and top magnetic shield cage section.
Figure 17D:
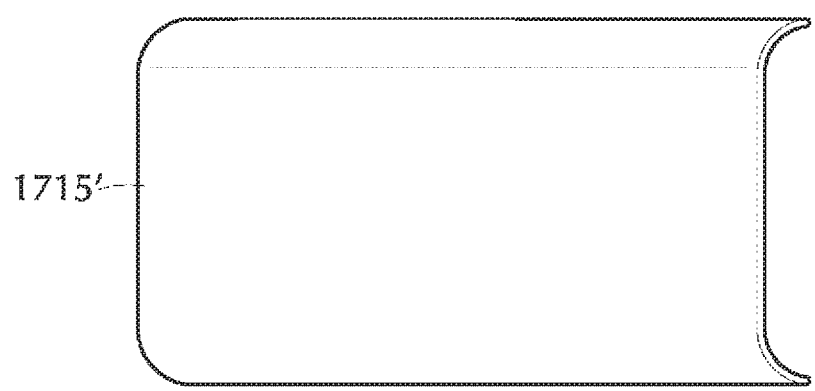
FIG. 17D is a bottom view of the battery tray and top magnetic shield cage section of FIG. 17C.

FIG. 17 is an exploded view of the battery door assembly 1575 of the integrated locator/indicator tool 1405. Preferably, the integrated locator/indicator tool 1405 is powered by batteries, most preferably, off-the-shelf (non-customized) batteries such as two CR123 lithium batteries 1705. The battery door assembly 1575 is removable, for example slideable within a complementary track defined in the outer housing section 1510. The batteries 1705 are received within a battery tray 1710 having appropriate electrical contacts. As mentioned above, batteries 1705 within the battery tray 1710 are encased in a magnetic shield cage. When assembled, the batteries are therefore completely surrounded or enclosed in the magnetic shield cage everywhere, except where necessary wiring of the battery terminals to the controller circuit printed circuit board 1573. Alternatively, partial shielding (e.g., less than complete or full enclosure) of the batteries in the magnetic shield cage is also contemplated. FIG. 17A is a cross-sectional view of the integrated location/indication tool 1405 along lines 17-17 in FIG. 17. In this cross-sectional view the magnetic shield cage surrounds the batteries 1705. It is seen in FIG. 17A that the magnetic shield cage comprises a bottom magnetic shield cage section 1715 and a top magnetic shield cage section 1720. Bottom magnetic shield cage section 1715 (FIGS. 17C & 17D) comprises two planar sections 1715', 1715" substantially perpendicular to one another. While the top magnetic shield cage section 1720, shown in FIG. 17B, has a top planar section that is bent or curved downward along is respective longitudinal sides parallel with the longitudinal axis of the batteries. Both ends of the longitudinal sides of the top magnetic shield cage section 1720 in an axial direction remain open. Battery tray 1710 having two terminal ends is mounted to the bottom magnetic shield cage section 1715 between the bent longitudinal sides (FIGS. 17C & 17D). The battery tray 1710 is oriented so that its planar surface in a longitudinal direction between the opposing terminals is substantially parallel with one of the planar sections 1715', while the plane intersecting one side of the terminal ends of the battery tray are substantially parallel with the other planar section 1715".

Figure 18A:
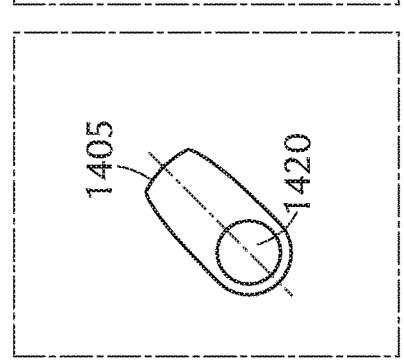
FIGS. 18A-18I are sequential illustrations of the steps for operating the electronic tools in accordance with the present invention.
Figure 18B:
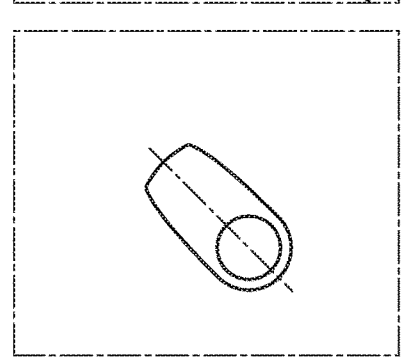
Figure 18C:
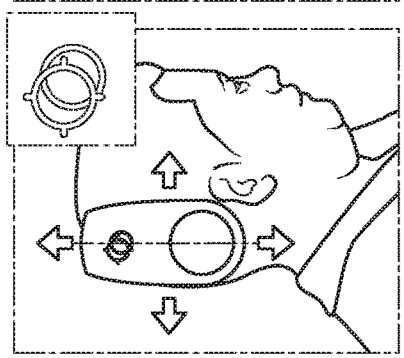
Figure 18D:
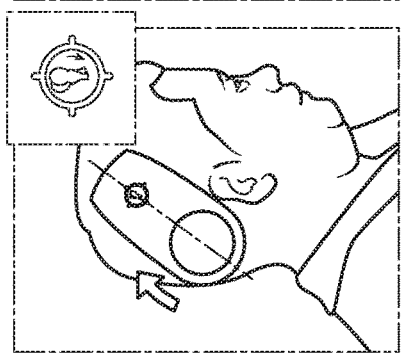
Figure 18E:
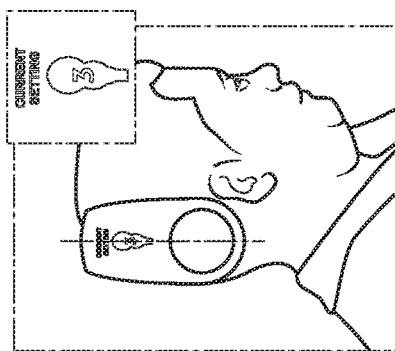
Figure 18F:
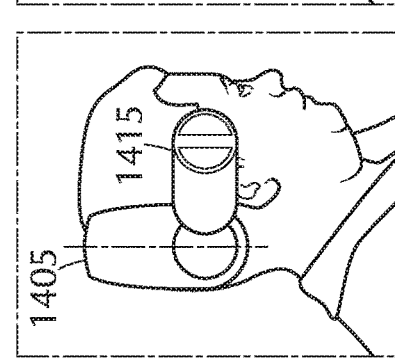
Figure 18G:
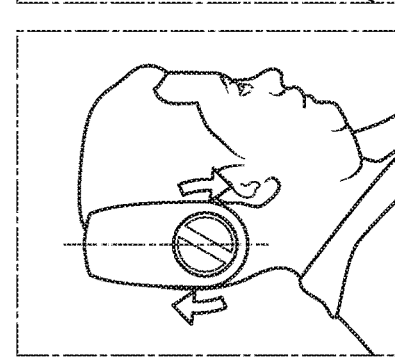
Figure 18H:
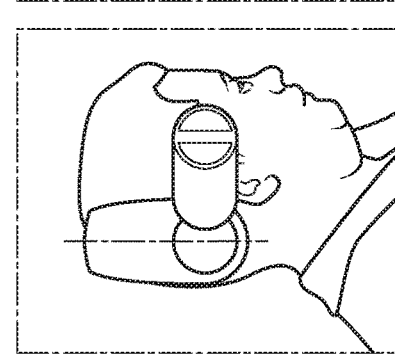
Figure 18I:
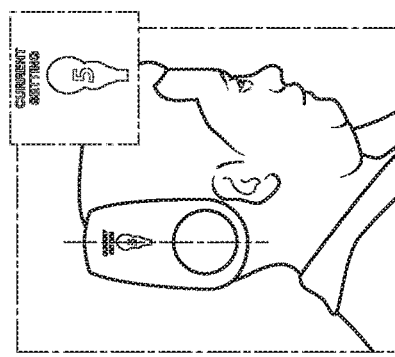

FIGS. 18A-18I are sequential steps in operating the improved electronic toolset of FIG. 14 in accordance with the present invention. In FIG. 18A the integrated locator/indicator tool 1405 is powered on by pressing the power button 1560. Holding the power button 1560 for a predetermined period of time, e.g., approximately 3 seconds, calibrates/clears or zeros out the magnetic field of the integrated locator/indicator tool 1405, as illustrated in FIG. 18B. Such calibration may be done following the expiration of the predetermined period of time in which the power button is held, after pushing another button, or automatically calibrated (not requiring that a button be pushed/held once the tool is powered on). Then a bottom surface (sensor floor) of the integrated locator/indicator tool 1405 is positioned against the skin above the implantable valve system such that the implantable valve is received in the complementary size and shaped recess 1520 defined in the exterior surface of the bottom housing section 1505, as illustrated in FIG. 18C. The integrated location/indication tool 1405 is moved in the appropriate direction (as indicated by the four arrows pointing in different directions) until the two circular visual images viewed on the LCD display 1555 are aligned with one another, indicating that the center of the adjustable valve unit 100 has been located. In parallel to or sequentially after having located the center of the adjustable valve unit 100, in FIG. 18D, the integrated locator/indicator tool 1405 is rotated until the two visual icons (complementary in shape (key hole shaped) to the implantable valve) displayed within the two circular visual images are aligned with one another to orient the integrated location/indication tool 1405 in the proper direction of flow of the implantable valve. It is now that the integrated location/indication tool 1405 has been centered and oriented in a direction of flow of the implantable valve, that the current indication or valve setting is read and visually displayed on the display (e.g., LCD) 1555 (FIG. 18E). If the current valve setting is to be changed or reprogrammed to a new valve setting, then in FIG. 18F the adjustment tool 1415 is inserted into the cavity 1420 of the integrated location/indication tool 1405 and rotated until the reference marking on the adjustment tool 1415 is aligned with the marking on the top lens 1540 corresponding to the read current device setting. In FIG. 18G the adjustment tool 1415 is rotated until the marking on the top lens is aligned with the marking representing the new valve setting. Once set to the new valve setting, in FIG. 18H the adjustment tool 1415 is removed from the integrated locator/indicator tool 1405 (while the integrated location/indication tool 1405 remains stationary in place) and this new valve setting is now automatically detected by the integrated location/indication tool 1405 and visibly displayed on the LCD 1555 (FIG. 18I). It is noted that the positioning of the integrated location/indication tool 1405 remains unchanged in steps 18E-18I. The improved electronic toolset eliminates the requirement or need to have to once again locate the center of the valve and then confirm the new valve setting following adjustment by the adjustment tool 1415.

The present inventive improved toolset for use in programming an implantable valve has been described and shown as including an integrated location/indication tool. It is contemplated and within the intended scope of the present invention for the none, some, or all of the tools in the tool set wherein the batteries are disposed in the magnetic shield cage, similar to that discussed in detail above, to prevent influence of residual magnetic fields from impacting on the sensor array present in the indicator tool. Furthermore, the present invention has been shown and described for encasing in a magnetic shield the batteries, but is equally suited for other ferromagnetic system components.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method of using an electronic toolset for locating, reading, adjusting and confirming adjustment of an implantable bodily fluid drainage system without requiring recalibration following adjustment, wherein the implantable bodily fluid drainage system includes an implantable bodily fluid drainage valve having an adjustable valve unit, the method comprising the steps of:

adjusting the adjustable valve unit from a current valve setting to a new valve setting using an adjustment tool in the electronic toolset, wherein the adjustment tool has at least one magnetic element; wherein an indicator tool in the electronic toolset reads or confirms the current valve setting using a sensor array; and wherein the indication tool also includes a ferromagnetic system component disposed in a magnet shield cage made of a metallic alloy having a permeability $\mu_z \geq$ approximately $1.0 \times 10^{-4}$ to prevent magnetic fields produced by the at least one magnetic element in the adjustment tool during the adjusting step from influencing the sensor array.

2. The method in accordance with claim 1, wherein the magnet shield cage at least partially shields the ferromagnetic system component.

3. The method in accordance with claim 1, wherein the magnet shield cage comprises a plurality of magnetic shield cage sections that when assembled forms an enclosure about the ferromagnetic system component, the enclosure forming two closed terminating ends.

4. The method in accordance with claim 3, wherein the plurality of magnetic shield cage sections comprises a bottom magnetic shield cage section and a top magnetic shield cage section.

5. The method in accordance with claim 4, wherein the bottom magnetic shield cage section comprises a first planar section and a second planar section substantially perpendicular to the first planar section; and wherein the top magnetic shield cage section comprises a substantially planar central section opposing sides in a longitudinal direction of the substantially planar central section being bent in the same direction.

6. The method in accordance with claim 1, wherein the ferromagnetic system component is at least one battery receivable in a tray having electrical contact terminals disposed at each terminating end in a longitudinal direction, the tray being attached to the first planar section of the bottom magnetic shield cage section while one terminating end of the electrical faces the second planar section of the bottom magnetic shield cage section.

7. The method in accordance with claim 1, wherein the electronic toolset further includes a locator tool for locating a center and/or orientation of the adjustable valve unit.

8. The method in accordance with claim 7, wherein at least two tools in the toolset are integrated into a single device.

9. The method in accordance with claim 7, wherein the locator tool of the electronic toolset does not have any openings through which the implantable bodily fluid drainage valve is manually palpated, rather all information regarding the center and/or orientation of the adjustable valve unit is provided via electronic feedback.

10. The method in accordance with claim 1, wherein the metallic alloy is a permalloy comprising approximately 80% nickel and approximately 20% iron content.

11. An electronic toolset for locating, reading, adjusting and confirming adjustment of an implantable bodily fluid drainage system without requiring recalibration following adjustment, wherein the implantable bodily fluid drainage system comprises an implantable bodily fluid drainage valve having an adjustable valve unit, the electronic toolset including:
an adjustment tool having at least one magnetic element for adjusting the adjustable valve unit from a current valve setting to a new valve setting;
an indication tool for reading the current valve setting or confirming a new valve setting using a sensor array; the indication tool further including a ferromagnetic system component disposed in a magnet shield cage made of a metallic alloy having a permeability $\mu z \geq$ approximately $1.0 \times 10^4$ to prevent residual magnetic fields produced by the plurality of magnets in the adjustment tool from influencing the sensor array.

12. The electronic toolset in accordance with claim 11, wherein the magnet shield cage comprises a plurality of magnetic shield cage sections that when assembled forms an enclosure about the ferromagnetic system component, the enclosure forming two closed terminating ends.

13. The electronic toolset in accordance with claim 12, wherein the plurality of sections comprises a bottom magnetic shield cage section and a top magnetic shield cage section.

14. The electronic toolset in accordance with claim 13, wherein the bottom magnetic shield cage section comprises a first planar section and a second planar section substantially perpendicular to the first planar section; and wherein the top magnetic shield cage section comprises a substantially planar central section opposing sides in a longitudinal direction of the substantially planar central section being bent in the same direction.

15. The electronic toolset in accordance with claim 11, wherein the ferromagnetic system component is at least one battery receivable in a tray having electrical contact terminals disposed at each terminating end in a longitudinal direction, the tray being attached to the first planar section of the bottom magnetic shield cage section while one terminating end of the electrical faces the second planar section of the bottom magnetic shield cage section.

16. The electronic toolset in accordance with claim 11, wherein the electronic toolset further includes a locator tool for locating a center and/or orientation angle of the adjustable valve unit.

17. The electronic toolset in accordance with claim 16, wherein at least two tools in the electronic toolset are integrated into a single device.

18. The electronic toolset in accordance with claim 11, wherein the locator tool of the electronic toolset does not have any openings through which the implantable bodily fluid drainage valve is manually palpated, rather all information regarding the center and/or orientation of the adjustable valve unit is provided via electronic feedback.

19. The electronic toolset in accordance with claim 11, wherein the metallic alloy is a permalloy comprising approximately 80% nickel and approximately 20% iron content.

* * * * *